United States Patent
Qian et al.

(10) Patent No.: US 12,428,391 B2
(45) Date of Patent: Sep. 30, 2025

(54) DIMETHYLSULFOXIMINE DERIVATIVE

(71) Applicant: CISEN PHARMACEUTICAL CO., LTD, Shandong (CN)

(72) Inventors: Wenyuan Qian, Shanghai (CN); Yonggang Liao, Shanghai (CN); Changqing Wei, Shanghai (CN); Zhengying Xi, Shanghai (CN); Yao Xiao, Shanghai (CN); Shuhui Chen, Shanghai (CN)

(73) Assignee: CISEN PHARMACEUTICAL CO., LTD, Shandong (CN)

( * ) Notice: Subject to any disclaimer, the term of this patent is extended or adjusted under 35 U.S.C. 154(b) by 550 days.

(21) Appl. No.: 18/009,440

(22) PCT Filed: Jun. 7, 2021

(86) PCT No.: PCT/CN2021/098601
§ 371 (c)(1),
(2) Date: Dec. 9, 2022

(87) PCT Pub. No.: WO2021/249337
PCT Pub. Date: Dec. 16, 2021

(65) Prior Publication Data
US 2023/0219920 A1    Jul. 13, 2023

(30) Foreign Application Priority Data

Jun. 11, 2020 (CN) .................. 202010528855.7
Aug. 5, 2020 (CN) .................. 202010779149.X

(51) Int. Cl.
*C07D 333/34* (2006.01)
*A61P 19/06* (2006.01)
*C07D 277/36* (2006.01)

(52) U.S. Cl.
CPC ............ *C07D 333/34* (2013.01); *A61P 19/06* (2018.01); *C07D 277/36* (2013.01)

(58) Field of Classification Search
CPC .. C07D 333/36; C07D 333/34; C07D 277/54; C07D 277/36
See application file for complete search history.

(56) References Cited

U.S. PATENT DOCUMENTS

| 6,166,064 A | 12/2000 | Dombroski et al. |
| 2019/0359564 A1 | 11/2019 | O'Neill et al. |
| 2020/0087270 A1 | 3/2020 | Franchi et al. |

FOREIGN PATENT DOCUMENTS

| CN | 1245490 A | 2/2000 |
| CN | 107428696 A | 12/2017 |
| CN | 111094243 A | 5/2020 |
| WO | WO-2016131098 A1 | 8/2016 |
| WO | WO-2017184604 A1 | 10/2017 |
| WO | WO-2017184624 A1 | 10/2017 |
| WO | WO-2018015445 A1 | 1/2018 |
| WO | WO-2019023147 A1 | 1/2019 |
| WO | WO-2019025467 A1 | 2/2019 |
| WO | WO-2019034686 A1 | 2/2019 |
| WO | WO-2019034690 A1 | 2/2019 |
| WO | WO-2019121691 A1 | 6/2019 |
| WO | WO-2019166619 A1 | 9/2019 |
| WO | WO-2020011731 A1 | 1/2020 |

OTHER PUBLICATIONS

Sep. 1, 2021 International Search Report issued in International Patent Application No. PCT/CN2021/098601.
Sep. 1, 2021 Written Opinion of the International Searching Authority issued in International Patent Application No. PCT/CN2021/098601.
Aug. 11, 2023 Chinese Office Action and search report issued in Chinese Patent Application No. 2021800413784.
Jan. 9, 2024 Notice of Reasons for Refusal in Japanese Application No. 2022-575974.
Aug. 6, 2024 Extended Search Report issued in European Patent Application No. EP21820982.

*Primary Examiner* — Valerie Rodriguez-Garcia
(74) *Attorney, Agent, or Firm* — Harness, Dickey & Pierce, P.L.C.

(57) ABSTRACT

Disclosed in the present invention is a series of dimethylsulfoximine derivatives, and specifically disclosed are a compound represented by formula (II) and a pharmaceutically acceptable salt thereof.

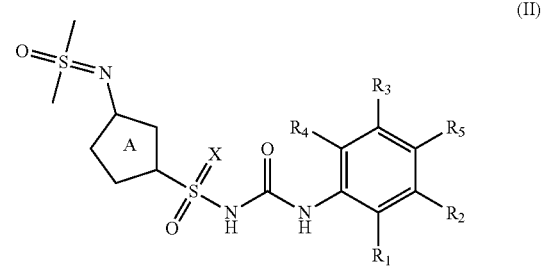

20 Claims, 1 Drawing Sheet

DIMETHYLSULFOXIMINE DERIVATIVE

CROSS-REFERENCE TO RELATED APPLICATIONS

The present application is a U.S. National Phase Application under 35 U.S.C. 371 of International Application No. PCT/CN2021/098601, filed on Jun. 7, 2021, which claims the benefit of Chinese Patent Application No. 202010528855.7, filed on Jun. 11, 2020 and Chinese Patent Application No. 202010779149.X, filed on Aug. 5, 2020.

TECHNICAL FIELD

The present disclosure relates to a series of dimethylsulfoximine derivatives, and specifically relates to a compound represented by formula (II) and a pharmaceutically acceptable salt thereof.

BACKGROUND

Inflammation is the basis for the occurrence and development of various diseases, and maintaining the balance of inflammatory responses is of great significance for the prevention and treatment of infection, autoimmune diseases and cancer, etc. Inflammasome plays an important role in the occurrence and development of inflammation-associated diseases, and the nucleotide-binding oligomerization domain (NOD)-like receptor family pyrin domain-containing protein 3 (NOD-like receptor family, pyrin domain-containing protein 3, NLRP3) inflammasome is able to be activated by a variety of pathogen-associated molecular patterns (PAMPs) and damage-associated molecular patterns (DAMPs), which in turn activates caspase-1 and releases mature forms of the proinflammatory cytokine interleukin IL-1β and IL-18 causing inflammatory responses in the body, and although this response can be used to defend against foreign pathogens, it is known that the abnormal or chronic activation of the NLRP3 inflammasome will cause downstream negative effects as well as the onset and progression of many diseases.

NLRP3 inflammasome is a macromolecular multiprotein complex with a molecular weight of about 700 kDa composed of nucleotide-binding oligomerization domain-like receptors (NLRs) family member NLRP3, adaptor protein ASC (apoptosis-associated speck-like protein containing a CARD) and the effector protein Caspase-1. It can be detected in a variety of immune cells such as granulocytes, macrophages, dendritic cells, B cells and non-immune cells such as epithelial cells and keratocytes, and its core protein NLRP3 is composed of 11 leucine repeat sequences (LRR) at the C-terminal, a NACHT domain in the middle and a Pyrin domain (PYD) at the N-terminal. NLRP3 interacts with the adaptor protein ASC through the PYD domain, and then ASC recruits and activates pro-Caspase-1 through its CARD domain to form a protein complex, that is, NLRP3 inflammasome. The recruited pro-Caspase-1 forms a heterotetramer through self-cleavage and hydrolysis, that is, the active form of Caspase-1. The active form of Caspase-1 cleaves cytokine precursors pro-IL-1β and pro-IL-18 to produce mature proinflammatory cytokines IL-1β and IL-18, which are then secreted extracellularly, thereby promoting the occurrence of inflammatory responses.

The activation of NLRP3 inflammasome requires two signals: priming and activation. During the priming phase, the transcription factor NF-κB is activated by TLR or TNF receptors, thereby up-regulating the expression of NLRP3 as well as IL-1β/IL-18 precursors, providing material reserves for the activation phase. During the activation phase, a variety of exogenous microorganisms or endogenous danger signals can act as activators, such as hyperglycemia, hyperlipidemia, uric acid crystals, cholesterol crystals, β-amyloid and microbial toxins. These activators can effectively induce the assembly of NLRP3 inflammasome by inducing mitochondrial damage, potassium ion efflux, and intracellular calcium ion concentration increase, and then activate NLRP3 inflammasome to mediate inflammatory response.

More and more studies have confirmed that NLRP3 inflammasome is closely related to the occurrence and development of various inflammatory diseases. NLRP3 inflammasome was first reported to be related to the onset of several familial genetic diseases, such as familial Mediterranean fever and Muckle-Wells syndrome. Later research found that the Cias1 gene encoding NLRP3 on chromosome 1 of these patients was mutated, so that NLRP3 could not be inhibited by itself and was always in an activated state; through the formation of NLRP3 inflammasome, cleaving pro-IL-1β and pro-IL-18 into mature IL-1β and IL-18, leading to their massive secretion and causing excessive inflammatory response in the body. The urate crystals in the joints and surrounding areas of gout patients swallowed by macrophages may activate the potassium ion efflux and induce mitochondria to produce a large amount of reactive oxygen species ROS, which activates the NLRP3 inflammasome and promotes the maturation and secretion of IL-1β. The downstream signal transduction factors are activated after the mature IL-1β binds to the IL-1 receptor of the target cells, which generate a large number of inflammatory mediators thereby aggravating the inflammatory response. Amyloid β-protein can cause inflammatory responses in the brain by activating the NLRP3 inflammasome of microglia, causing neuronal damage and death, which in turn can lead to neurodegenerative diseases such as Alzheimer's disease. Cholesterol taken by endothelial cells and macrophages from blood forms tiny cholesterol crystals, activates NLRP3 inflammasomes, and plays an important role in the occurrence and development of atherosclerosis. Long-term high concentration of glucose in the body can stimulate islet cells to activate NLRP3 inflammasome, produce mature IL-1β, trigger a series of inflammatory reactions, induce IL-1β-dependent cell injury and death, aggravate islet cell dysfunction, and finally lead to the occurrence and development of type II diabetes.

A variety of NLRP3 antagonists have been reported in patent applications such as WO2016131098, WO2019025467, WO2019121691 and WO2018015445. MCC950, a derivative of diaryl sulfonylurea, can reduce the severity of experimental autoimmune encephalomyelitis (EAE) in mice by inhibiting NLRP3 inflammasome activity. Another small molecule antagonist, CY-09, specifically blocks the assembly and activation of NLRP3 inflammasome and has significant therapeutic effects on cryopyrin-associated auto-inflammatory syndrome (cAPS) and type II diabete models in mice. IFM-2427, the NLRP3 antagonist of IFM-Tre, is undergoing multiple clinical phase I studies.

MCC950

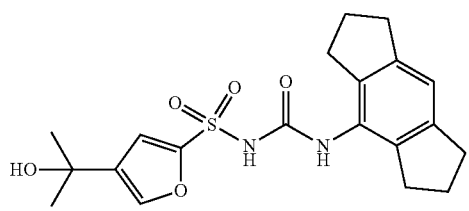

CY-09

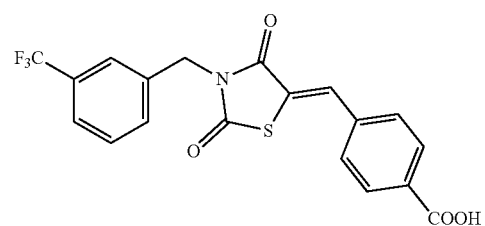

Exploring the activation mechanism of NLRP3 inflammasome and developing small molecule antagonists targeted NLRP3 can provide potential therapeutic means for related inflammatory diseases, which is of great significance and broad prospects. Currently, there is still a need to develop new NLRP3 antagonists for the treatment of inflammatory diseases.

CONTENT OF THE PRESENT INVENTION

The present disclosure provides a compound represented by formula (II) or a pharmaceutically acceptable salt thereof, (II)

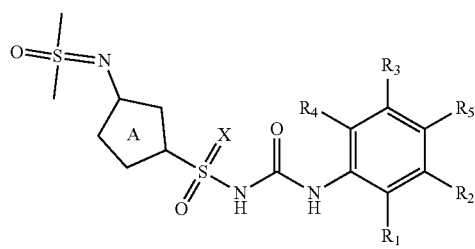

wherein, X is selected from O and $NR_b$;

$R_1$ and $R_4$ are each independently selected from H, $C_{1-3}$ alkyl, phenyl and 5- to 6-membered heteroaryl, and the $C_{1-3}$ alkyl, phenyl and 5- to 6-membered heteroaryl are optionally substituted with 1, 2 or 3 $R_a$;

$R_2$ and $R_3$ are each independently selected from H, $NH_2$, halogen and $C_{1-3}$ alkyl;

or $R_1$, $R_2$ together with the carbon atoms to which they are attached to form $C_{4-5}$ cycloalkyl and $C_{4-5}$ cycloalkenyl;

or $R_3$, $R_4$ together with the carbon atoms to which they are attached to form $C_{4-5}$ cycloalkyl and $C_{4-5}$ cycloalkenyl;

$R_5$ is selected from H, F, Cl, D and CN;

$R_a$ is each independently selected from H, $C_{1-3}$ alkoxy and CN;

$R_b$ is selected from H, CN and $C_{1-3}$ alkyl;

ring A is selected from 5-membered heteroaryl;

the 5- to 6-membered heteroaryl and 5-membered heteroaryl contain 1, 2, 3 or 4 heteroatoms or heteroatom groups independently selected from —NH—, —O—, —S— and N.

In some embodiments of the present disclosure, the compound has a structure represented by formula (II-1) or (II-2), (II-1)

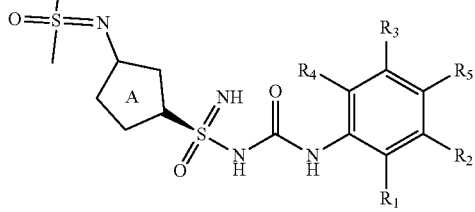

(II-2)

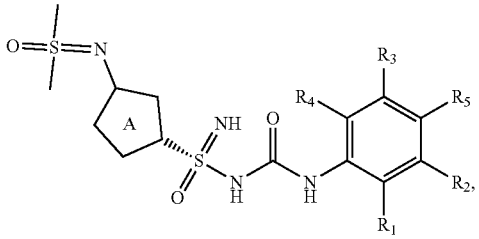

wherein, ring A, $R_1$, $R_2$, $R_3$, $R_4$ and $R_5$ are as defined in the present disclosure.

In some embodiments of the present disclosure, the compound has a structure represented by formula (I-a) or (II-a), (I-a)

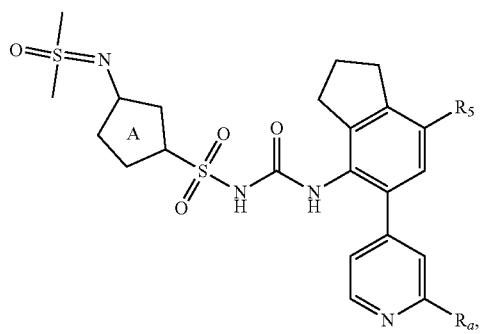

(II-a)

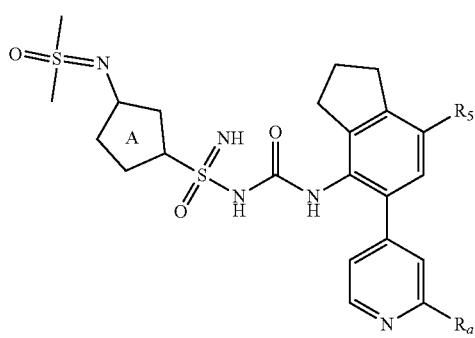

wherein, ring A, $R_a$ and $R_5$ are as defined in the present disclosure.

In some embodiments of the present disclosure, the compound has a structure represented by formula (I-b) or (II-b),

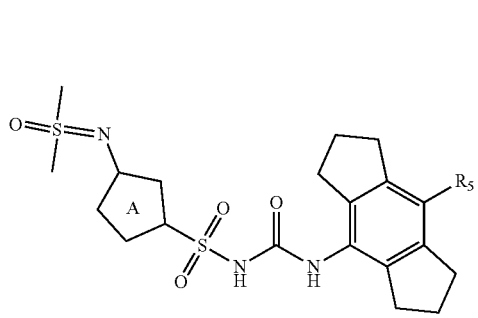
(I-b)

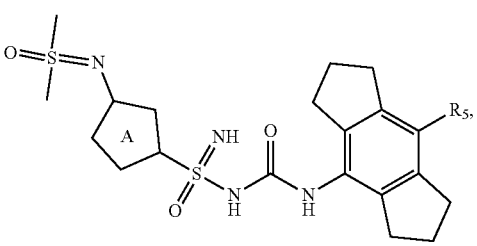
(II-b)

ring A and R$_5$ are as defined in the present disclosure.

In some embodiments of the present disclosure, the compound has a structure represented by formula (I-c) or (II-c),

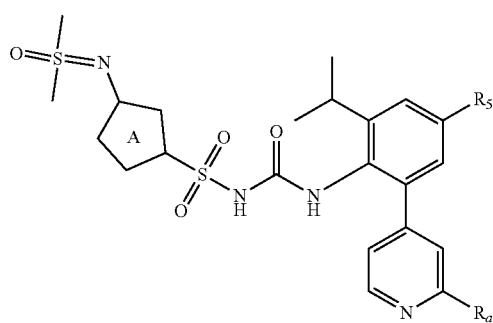
(I-c)

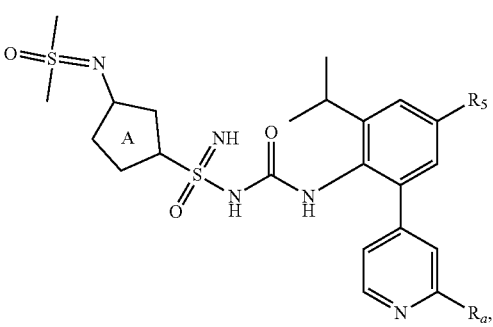
(II-c)

ring A, R$_a$ and R$_5$ are as defined in the present disclosure.

In some embodiments of the present disclosure, the compound has a structure represented by formula (III),

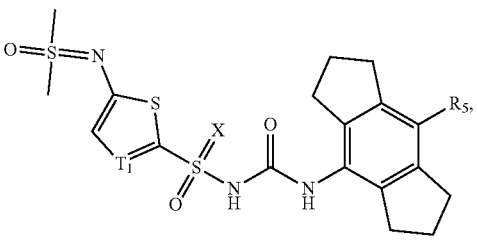
(III)

wherein,

T$_1$ is selected from N and CH;

X and R$_5$ are as defined in the present disclosure.

In some embodiments of the present disclosure, the R$_a$ is selected from H, OCH$_3$ and CN, and other variables are as defined in the present disclosure.

In some embodiments of the present disclosure, the R$_1$ is selected from

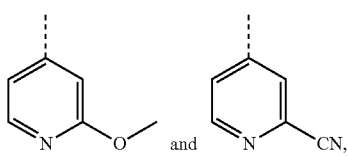

and other variables are as defined in the present disclosure.

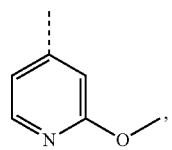

In some embodiments of the present disclosure, the R$_1$ is selected from and other variables are as defined in the present disclosure.

In some embodiments of the present disclosure, the R$_2$ is selected from H, and other variables are as defined in the present disclosure.

In some embodiments of the present disclosure, the R$_3$ is selected from H, and other variables are as defined in the present disclosure.

In some embodiments of the present disclosure, the R$_4$ is selected from and other variables are as defined in the present disclosure.

In some embodiments of the present disclosure, the R$_1$, R$_2$ together with the carbon atoms to which they are attached form

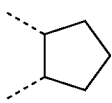 or 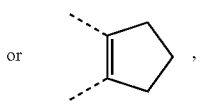, and other variables are as defined in the present disclosure.

In some embodiments of the present disclosure, the $R_3$, $R_4$ together with the carbon atoms to which they are attached form

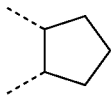 or 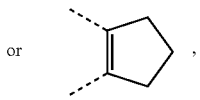, and other variables are as defined in the present disclosure.

In some embodiments of the present disclosure, the $R_1$, $R_2$ together with the carbon atoms to which they are attached form

, and other variables are as defined in the present disclosure.

In some embodiments of the present disclosure, the $R_3$, $R_4$ together with the carbon atoms to which they are attached form

, and other variables are as defined in the present disclosure.

In some embodiments of the present disclosure, the structural moiety

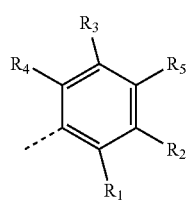

is selected from

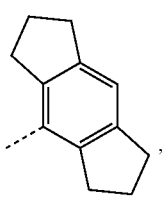

In some embodiments of the present disclosure, the structural moiety

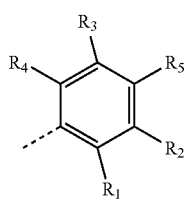

is selected from

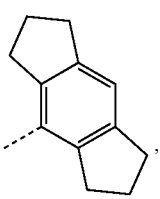

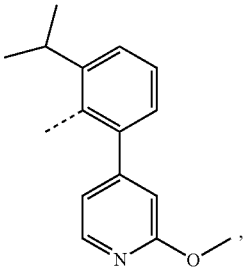

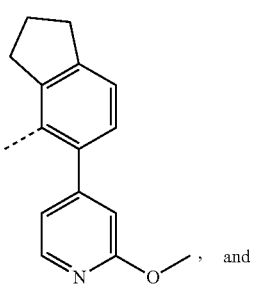, and

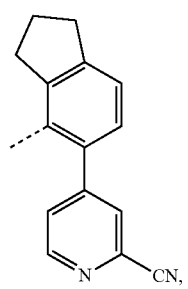

and other variables are as defined in the present disclosure.

In some embodiments of the present disclosure, the structural moiety

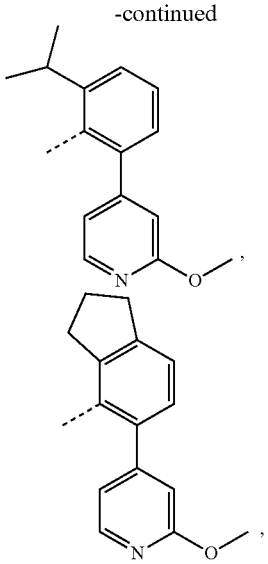

and other variables are as defined in the present disclosure.

In some embodiments of the present disclosure, the ring A is selected from thienyl and thiazolyl, and other variables are as defined in the present disclosure.

In some embodiments of the present disclosure, the ring A is selected from

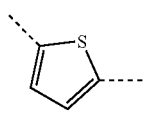 and 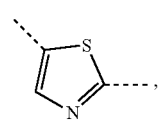, and other variables are as defined in the present disclosure.

In some embodiments of the present disclosure, the ring A is selected from

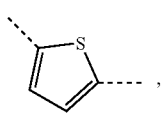, and other variables are as defined in the present disclosure.

The present disclosure provides a compound represented by formula (II) or a pharmaceutically acceptable salt thereof, (II)

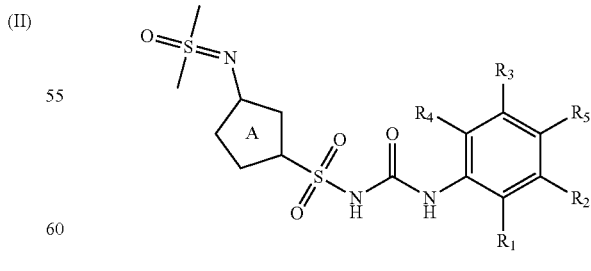

wherein,

X is selected from O and $NR_b$;

$R_1$ and $R_4$ are each independently selected from H, $C_{1-3}$ alkyl, phenyl and 5- to 6-membered heteroaryl, and the $C_{1-3}$ alkyl, phenyl and 5- to 6-membered heteroaryl are optionally substituted with 1, 2 or 3 $R_a$;

$R_2$ and $R_3$ are each independently selected from H, $NH_2$, halogen and $C_{1-3}$ alkyl;

or $R_1$, $R_2$ together with the carbon atoms to which they are attached to form $C_{4-5}$ cycloalkyl;

or $R_3$, $R_4$ together with the carbon atoms to which they are attached to form $C_{4-5}$ cycloalkyl;

$R_5$ is selected from H, F, Cl, D and CN;

$R_a$ is selected from H, $C_{1-3}$ alkoxy and CN;

$R_b$ is selected from H, CN and $C_{1-3}$ alkyl;

ring A is selected from 5-membered heteroaryl;

the 5- to 6-membered heteroaryl and 5-membered heteroaryl contain 1, 2, 3 or 4 heteroatoms or heteroatom groups independently selected from —NH—, —O—, —S— and N.

In some embodiments of the present disclosure, the compound has a structure represented by formula (II-1) or (II-2), (II-1)

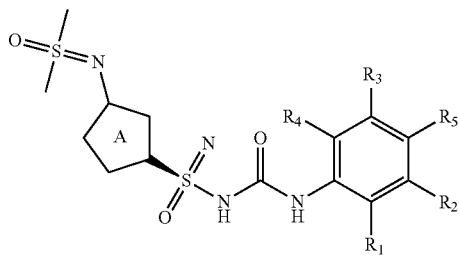

(II-2)

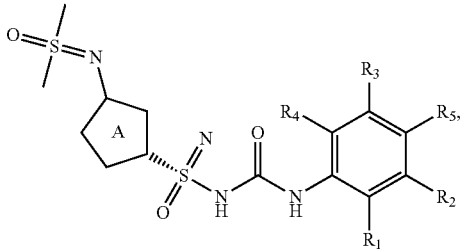

wherein, ring A, $R_1$, $R_2$, $R_3$, $R_4$ and $R_5$ are as defined in the present disclosure.

The present disclosure also provides a compound represented by formula (I) or a pharmaceutically acceptable salt thereof, (I)

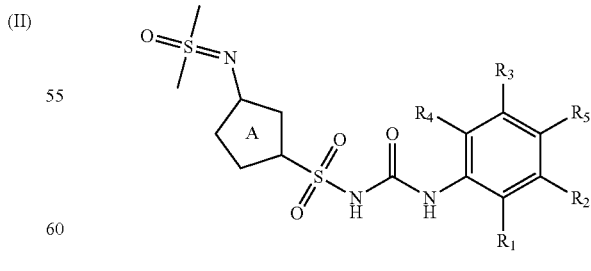

wherein, $R_1$ and $R_4$ are each independently selected from H, $C_{1-3}$ alkyl, phenyl and 5- to 6-membered heteroaryl, and the $C_{1-3}$ alkyl, phenyl and 5- to 6-membered heteroaryl are optionally substituted with 1, 2 or 3 $R_a$;

$R_2$ and $R_3$ are each independently selected from H, $NH_2$, halogen and $C_{1-3}$ alkyl;

or $R_1$, $R_2$ together with the carbon atoms to which they are attached to form $C_{4-5}$ cycloalkyl;

or $R_3$, $R_4$ together with the carbon atoms to which they are attached to form $C_{4-5}$ cycloalkyl;

$R_5$ is selected from H, F, Cl, D and CN;

$R_a$ is selected from H, $C_{1-3}$ alkoxy and CN;

ring A is selected from 5-membered heteroaryl;

the 5- to 6-membered heteroaryl and 5-membered heteroaryl contain 1, 2, 3 or 4 heteroatoms or heteroatom groups independently selected from —NH—, —O—, —S— and N.

There are still some embodiments of the present disclosure which are obtained by any combination of the above variables.

The present disclosure also provides a compound represented by the following formula or a pharmaceutically acceptable salt thereof,

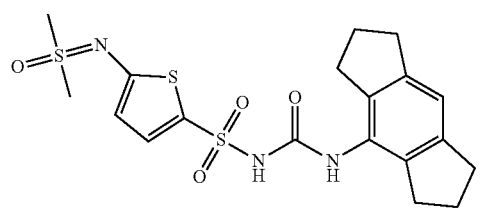

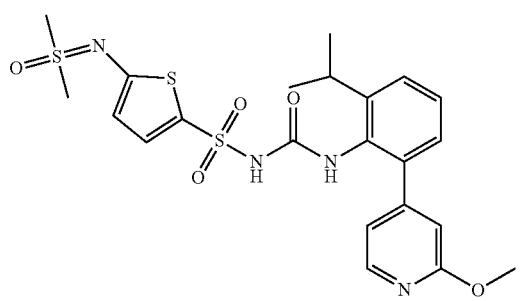

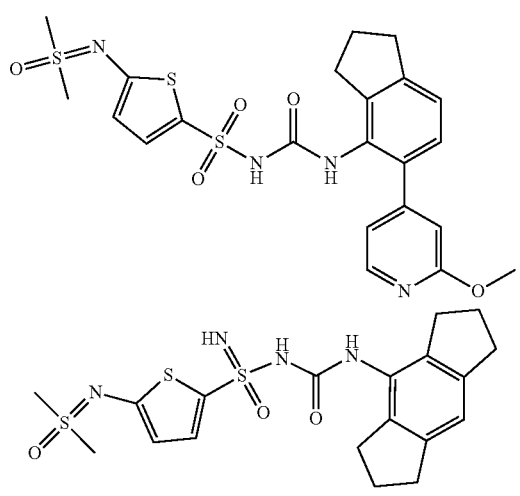

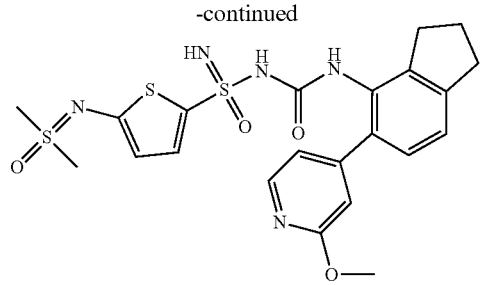

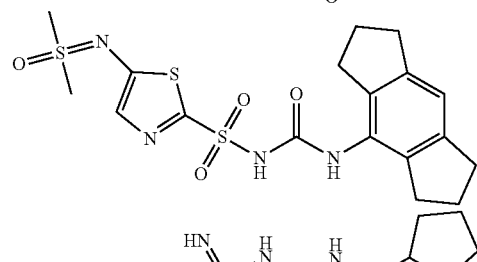

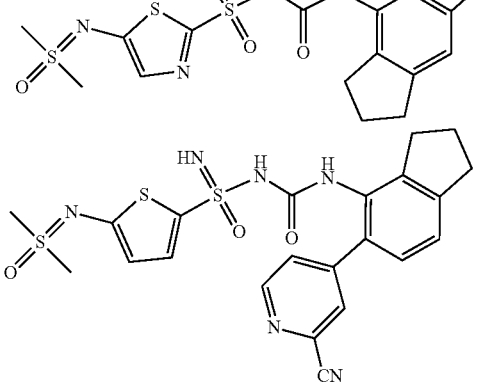

In some embodiments of the present disclosure, the compound or the pharmaceutically acceptable salt thereof is selected from,

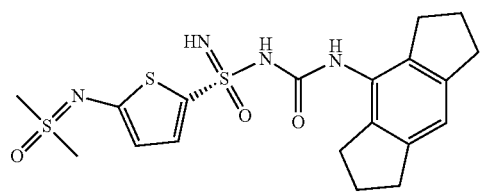

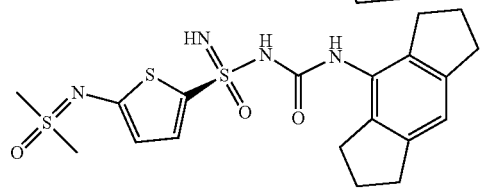

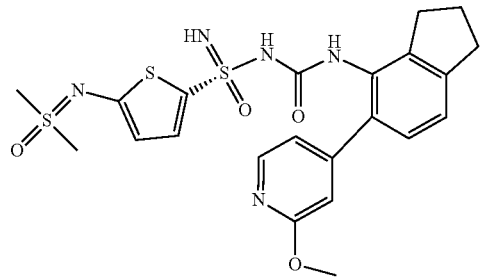

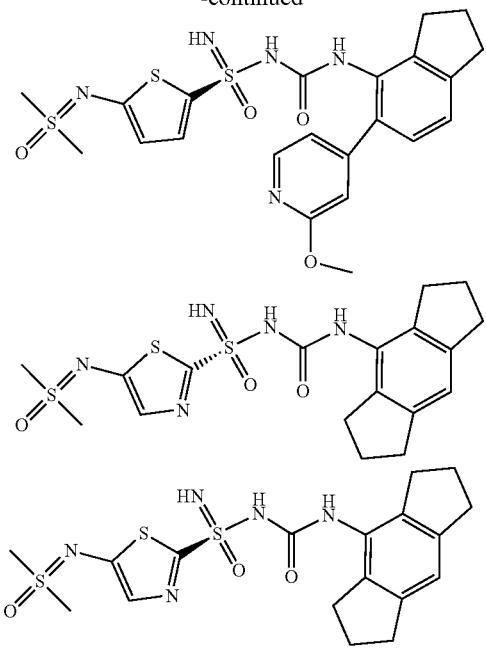

In some embodiments of the present disclosure, disclosed is a use of the compound or the pharmaceutically acceptable salt thereof in the manufacture of a medicament for the treatment of diseases related to NLRP3.

In some embodiments of the present disclosure, the use is characterized in that the medicament for the treatment of diseases related to NLRP3 antagonists is a medicament for the treatment of diseases related to inflammation.

Technical Effect

As NLRP3 antagonists, the compounds of the present disclosure exhibit good NLRP3 inhibitory activity, have good oral bioavailability and high exposure, and have good in vivo efficacy; the compounds showed good therapeutic effect on the MSU-induced Air Pouch gout model in C57BL/6 mice, and have the potential to treat gout and other diseases related to inflammatory cytokines, and have great application prospects.

Definition and Description

Unless otherwise specified, the following terms and phrases used herein have the following meanings. A specific term or phrase should not be considered indefinite or unclear in the absence of a particular definition, but should be understood according to the common meaning. When a trade name appears herein, it is intended to refer to its corresponding commercial product or active ingredient thereof.

The term "pharmaceutically acceptable" is used herein in terms of those compounds, materials, compositions, and/or dosage forms, which are suitable for use in contact with human and animal tissues within the scope of reliable medical judgment, without excessive toxicity, irritation, anaphylactic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by contacting the compound with a sufficient amount of a base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by contacting the compound with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, and racemic and other mixtures thereof, such as enantiomers or diastereomer enriched mixtures, all of which are within the scope of the present disclosure. Additional asymmetric carbon atoms may be present in substituents such as alkyl. All these isomers and their mixtures are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or "(±)" refers to racemic.

Unless otherwise specified, the absolute configuration of a stereogenic center is represented by a wedged solid bond (⧫) and a wedged dashed bond (⧫), and the relative configuration of a stereogenic center is represented by a straight solid bond (⧫) and a straight dashed bond (⧫) a wave line (⧫) is used to represent a wedged solid bond ( ) or a wedged dashed bond ( ), or the wave line ( ) is used to represent a straight solid bond ( ) or a straight dashed bond ( ).

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "substituted" means one or more than one hydrogen atom(s) on a specific atom are substituted by the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When the number of a substituent is vacant, it means that the substituent does not exist, for example, -A-(R)$_0$ means that the structure is actually -A.

When a substituent is vacant, it means that the substituent does not exist, for example, when X is vacant in A-X, the structure of A-X is actually A.

When one of the variables is selected from a single bond, it means that the two groups linked by the single bond are connected directly, for example, when L in A-L-Z represents a single bond, the structure of A-L-Z is actually A-Z.

When the bond of a substituent can be cross-connected to two or more atoms on a ring, the substituent can be bonded to any atom on the ring, for example, the structural unit

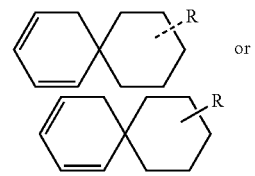

means that the substitution can be substituted with the substituent R at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

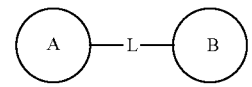

is -M-W—, then -M-W— can link ring A and ring B to form

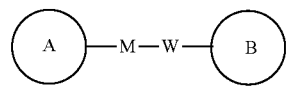

in the direction same as left-to-right reading order, and form

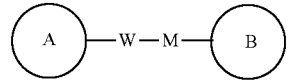

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (／), a straight dashed bond (／) or a wavy line

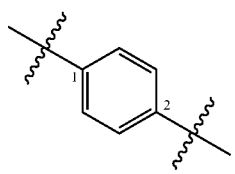 [SMILES: *c1ccc(*)cc1]

For example, the straight solid bond in —OCH₃ means that it is linked to other groups through the oxygen atom in the group; the straight dashed bonds in

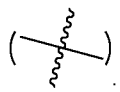

means that it is linked to other groups through the two ends of nitrogen atom in the group; the wave lines in

means that the phenyl group is linked to other groups through carbon atoms at position 1 and position 2;

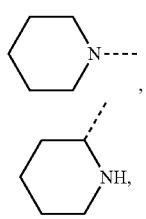

means that it can be linked to other groups through any linkable sites on the piperidinyl by one chemical bond, including at least four types of linkage, including

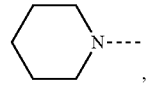

Even though the H atom is drawn on the —N—,

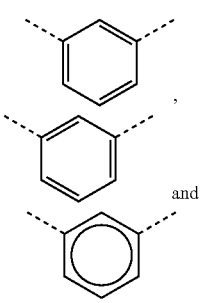

still includes the linkage of merely when one chemical bond was connected, the H of this site will be reduced by one to the corresponding monovalent piperidinyl.

Unless otherwise specified, the term "aromatic ring" means a cyclic group with a conjugated π-electron system in which the interatomic space is covered by an off-domain π electron cloud. In the structural formula, it can be written in the form of alternating single and double bonds when the atomic valence and covalent bonding rules are met, or

○ can be used to represent an off-domain π electron cloud. For example, the structure represented by structural formula are the same, and the structure represented by structural formula

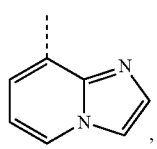

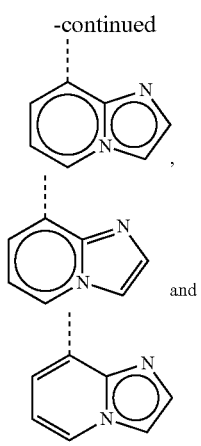
, and are the same. It can be a single ring or a fused polycyclic ring system in which each ring is aromatic. Unless otherwise specified, the ring optionally contains 0, 1 or more heteroatoms independently selected from O, S and N.

Unless otherwise specified, the number of atoms in a ring is usually defined as the number of ring members, for example, "5- to 7-membered ring" refers to a "ring" in which 5-7 atoms are arranged around.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "halo" or "halogen" by itself or as part of another substituent refers to fluorine, chlorine, bromine or iodine atom.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, "$C_{3-5}$ cycloalkyl" refers to a saturated cyclic hydrocarbon group consisting of 3 to 5 carbon atoms, which is a monocyclic system, and the $C_{3-5}$ cycloalkyl includes $C_{3-4}$ and $C_{4-5}$ cycloalkyl, etc.; it can be monovalent, divalent or multivalent. Examples of $C_{3-5}$ cycloalkyl include, but are not limited to, cyclopropyl, cyclobutyl, cyclopentyl, etc.

Unless otherwise specified, "$C_{4-5}$ cycloalkyl" refers to a saturated cyclic hydrocarbon group consisting of 4 to 5 carbon atoms, which is a monocyclic system; it can be monovalent, divalent or multivalent. Examples of $C_{4-5}$ cycloalkyl include, but are not limited to, cyclobutyl, cyclopentyl, etc.

Unless otherwise specified, the term "$C_{4-5}$ cycloalkenyl" refers to a partially unsaturated cyclic hydrocarbon group consisting of 4 to 5 carbon atoms containing at least one carbon-carbon double bond, which is a monocyclic system. The $C_{4-5}$ cycloalkenyl includes $C_4$ or $C_5$ cycloalkenyl; it can be monovalent, divalent or multivalent. Examples of $C_{4-5}$ cycloalkenyl include, but are not limited to, cyclobutenyl, cyclopentenyl, cyclopentadienyl, etc.

Unless otherwise specified, the terms "5- to 6-membered heteroaryl ring" and "5- to 6-membered heteroaryl" in the present disclosure can be used interchangeably, and the term "5- to 6-membered heteroaryl" refers to a monocyclic group consisting of 5 to 6 ring atoms with a conjugated π-electron system, and the 1, 2, 3 or 4 ring atoms of which are heteroatoms independently selected from O, S and N, and the rest are carbon atoms. Where the nitrogen atom is optionally quaternized, the nitrogen and sulfur heteroatoms can be optionally oxidized (i.e., NO and $S(O)_p$, wherein p is 1 or 2). The 5- to 6-membered heteroaryl can be attached to the rest of the molecule through a heteroatom or a carbon atom. The 5- to 6-membered heteroaryl includes 5-membered and 6-membered heteroaryl. Examples of the 5- to 6-membered heteroaryl groups include, but are not limited to, pyrrolyl (including N-pyrrolyl, 2-pyrrolyl and 3-pyrrolyl, etc.), pyrazolyl (including 2-pyrazolyl and 3-pyrrolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl or pyrimidyl (including 2-pyrimidyl and 4-pyrimidyl, etc.).

Unless otherwise specified, the term "5-membered heteroaryl" in the present disclosure refers to a monocyclic group consisting of 5 ring atoms with a conjugated π-electron system, and the 1, 2, 3 or 4 ring atoms of which are heteroatoms independently selected from O, S and N, and the rest are carbon atoms. Where the nitrogen atom is optionally quaternized, and the nitrogen and sulfur heteroatoms can be optionally oxidized (i.e., NO and $S(O)_p$, wherein p is 1 or 2). The 5-membered heteroaryl can be attached to the rest of the molecule through a heteroatom or a carbon atom. Examples of the 5-membered heteroaryl groups include, but are not limited to, pyrrolyl (including N-pyrrolyl, 2-pyrrolyl and 3-pyrrolyl, etc.), pyrazolyl (including 2-pyrazolyl and 3-pyrrolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furyl (including 2-furyl and 3-furyl, etc.), or thienyl (including 2-thienyl and 3-thienyl, etc.).

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvents used in the present disclosure are commercially available.

The present disclosure employs the following abbreviations: DMSO represents dimethyl sulfoxide; $CO_2$ represents carbon dioxide; ATP represents adenosine triphosphate; LPS represents lipopolysaccharide; CBA represents cytometric bead array; PMA represents phorbol 12-myristate 13-acetate; NEAA represents non-essential amino acid; FBS represents fetal bovine serum; IL-1β represents interleukin-1β; Human IL-1β Flex Set represents human interleukin-1β detection kit.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

Figure 1:
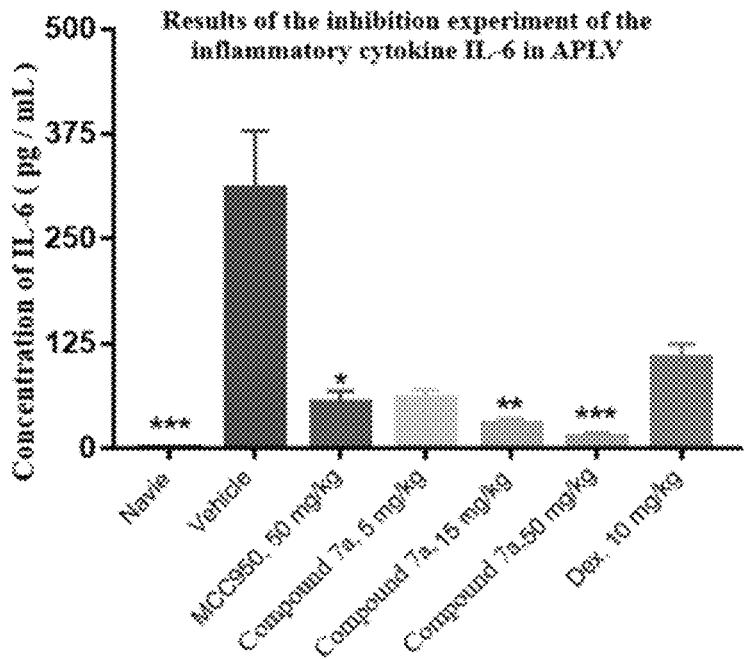
FIG. 1: Results of the inhibition experiment of the inflammatory cytokine IL-6 in APLV.

The present disclosure is described in detail by the embodiments below, but it does not mean that there are any adverse restrictions on the present disclosure. The present disclosure has been described in detail herein, and its specific embodiments have also been disclosed; for one skilled in the art, it is obvious to make various modifications and improvements to the embodiments of the present disclosure without departing from the spirit and scope of the present disclosure.

Embodiment 1

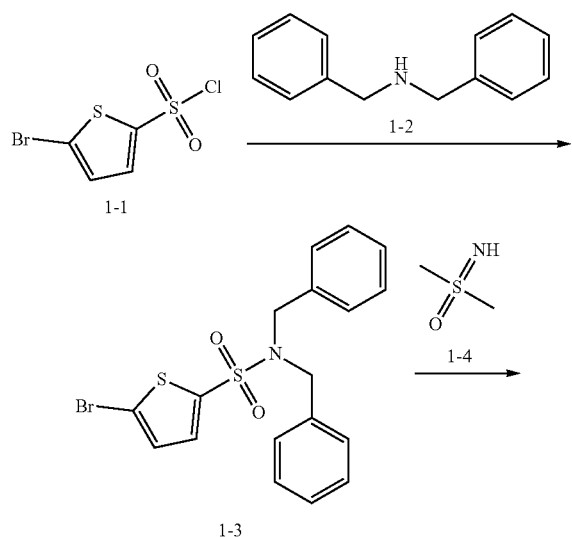

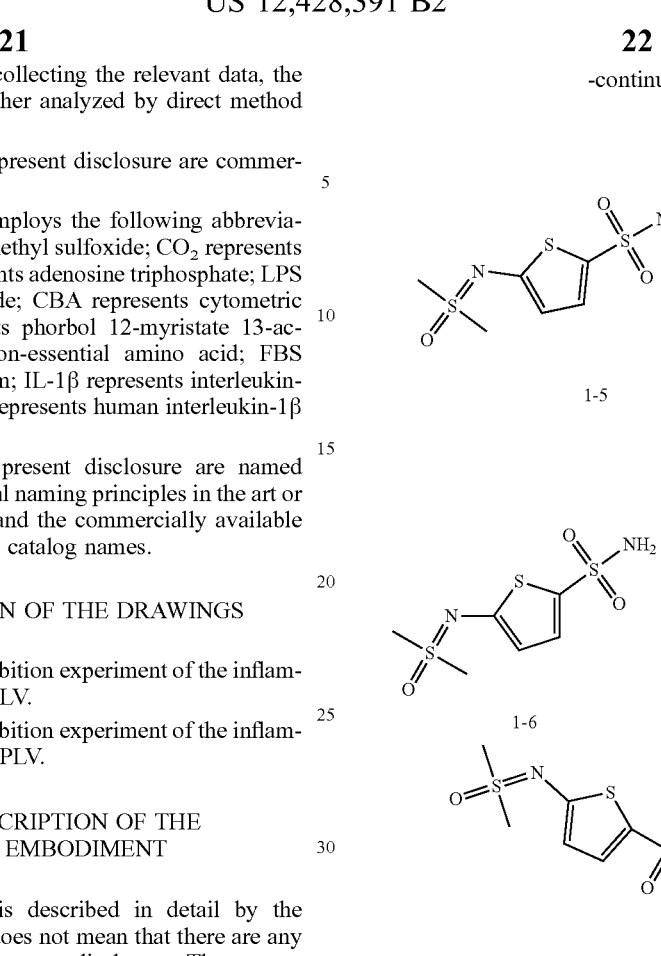

Step 1: Compound 1-1 (3.2 g, 12.2 mmol) and triethylamine (1.9 g, 18.4 mmol) were dissolved in dichloromethane (100 mL), then compound 1-2 (2.66 g, 13.46 mmol) was added, and the reaction was stirred at 25° C. for 2 hours. The reaction mixture was concentrated after the reaction was completed, and then the crude product was separated by column chromatography (petroleum ether:ethyl acetate=3:1) to obtain compound 1-3. MS ESI calculated for $C_{18}H_{16}BrNO_2S_2$ [M+H, M+H+2]$^+$ 422, 424, found 422, 424.

Step 2: Compound 1-3 (2.8 g, 22.6 mmol) was dissolved in dioxane (30 mL), and then 2-(di-tert-butylphosphino)biphenyl (282.6 mg, 947.1 μmol), compound 1-4 (661.6 mg, 7.1 mmol), sodium tert-butoxide (682.6 mg, 7.1 mmol) and tris(dibenzylideneacetone)dipalladium (433.6 mg, 473.5 μmol) were added, stirred at 80° C. for 1 hour. The reaction mixture was cooled and filtered after the reaction was completed, and the filtrate was concentrated, and then the crude product was purified by column chromatography (petroleum ether:ethyl acetate=3:1) to obtain compound 1-5. MS ESI calculated for $C_{20}H_{22}N_2O_3S_3$ [M+H]$^+$ 435, found 435.

Step 3: Compound 1-5 (1.0 g, 2.3 mmol) was dissolved in dichloromethane (10 mL), and sulfuric acid (concentration of 98%, 3.5 mL) was added dropwise at 0° C., and the reaction mixture was stirred at 25° C. for 1 hour, and then poured into ice water (50 mL), then extracted with dichloromethane (150 mL). The organic phase was concentrated, and the crude product was purified by column chromatography (petroleum ether:ethyl acetate=1:1) to obtain compound 1-6. MS ESI calculated for $C_6H_{10}N_2O_3S_3$ [M+H]$^+$ 255, found 255.

Step 4: Sodium hydride (30.3 mg, 758.3 µmol, purity of 60%) was added to a solution of compound 1-6 (150.0 mg, 589.7 µmol) in tetrahydrofuran (10 mL), stirred at 0° C. for 10 min, and then a solution of compound 1-7 (123.3 mg, 619.2 µmol) in tetrahydrofuran (10 mL) was added to the system and stirred at 25° C. for 0.5 hours. The reaction was quenched with dilute hydrochloric acid (1 mol/L, 1 mL) after the reaction was completed, then extracted with ethyl acetate (50 mL*2). The organic phase was concentrated, and the crude product was purified by column chromatography (ethyl acetate:ethanol=10:1) to obtain compound 1. MS ESI calculated for $C_{19}H_{23}N_3O_4S_3$ [M+H]$^+$ 454, found 454. $^1$H NMR (400 MHz, CD$_3$CN) δ ppm 8.42 (brs, 1H), 8.19 (s, 1H), 8.09 (s, 1H), 7.01 (d, J=4.0 Hz, 1H), 6.38 (d, J=4.0 Hz, 1H), 3.23 (s, 6H), 2.87 (brt, J=7.4 Hz, 4H), 2.66 (brt, J=7.4 Hz, 4H), 2.00-2.07 (m, 4H).

Embodiment 2

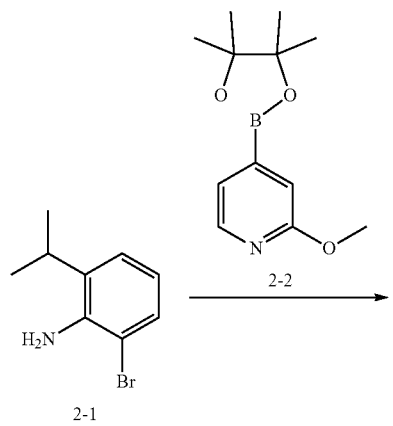

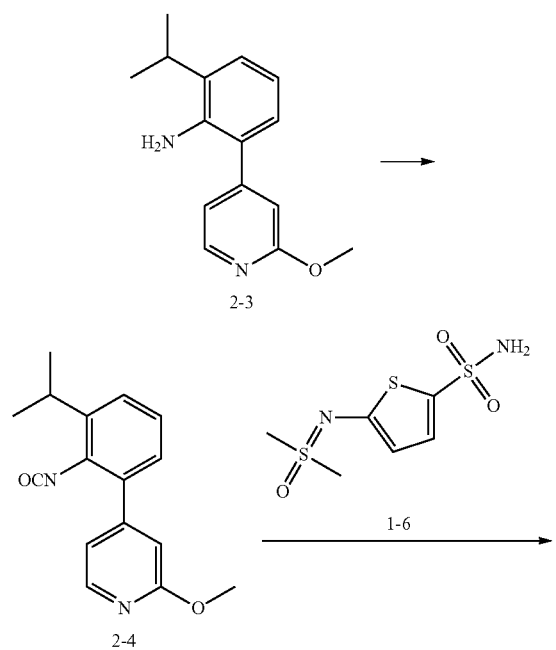

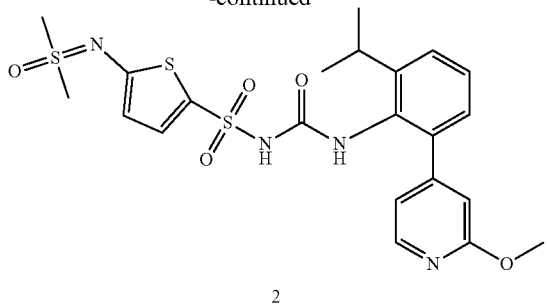

2

Step 1: Compound 2-1 (500.0 mg, 2.3 mmol) and compound 2-2 (357.0 mg, 2.3 mmol) were dissolved in dioxane (40 mL)/water (8 mL), and then [1,1'-bis(diphenylphosphino)ferrocene]dichloropalladium(II) dichloromethane complex (191.1 mg, 234.0 µmol) and potassium carbonate (646.8 mg, 4.7 mmol) were added, and the reaction was stirred at 100° C. for 2 hours, then cooled to room temperature, extracted with water (50 mL) and ethyl acetate (150 mL). The organic phase was dried over anhydrous sodium sulfate and concentrated, and the crude product was purified by column chromatography (petroleum ether:ethyl acetate=10:1) to obtain compound 2-3. MS ESI calculated for $C_{15}H_{18}N_2O$ [M+H]$^+$ 243, found 243.

Step 2: Compound 2-3 (95.0 mg, 392.1 mmol) was dissolved in tetrahydrofuran (10 mL), and then triphosgene (50.0 mg, 168.6 µmol) and triethylamine (119.0 mg, 1.2 mmol) were added at 25° C., and the reaction was stirred at 25° C. for 0.5 hours. After the reaction was completed, the reaction mixture was filtered to obtain a solution of compound 2-4 in tetrahydrofuran, which was directly used in the next step. MS ESI calculated for $C_{16}H_{16}N_2O_2$ [M+H]$^+$ 269, found 269.

Step 3: Sodium hydride (39.3 mg, 982.9 µmol, purity of 60%) was added to a solution of compound 1-6 (100.0 mg, 393.2 µmol) in tetrahydrofuran (10 mL), stirred at 0° C. for 10 min, and then a solution of compound 2-4 (105.49 mg, 393.16 µmol) in tetrahydrofuran (10 mL) was added to the system and stirred at 25° C. for 0.5 hours. The reaction was quenched with dilute hydrochloric acid (1 mol/L, 1 mL) after the reaction was completed, then extracted with ethyl acetate (50 mL*2). The organic phase was concentrated, and the crude product was separated by preparative high performance liquid chromatography (chromatographic column: Welch Xtimate C18 150*25 mm*5 µm; mobile phase: [water (10 mM ammonium bicarbonate)-acetonitrile]; acetonitrile %: 15%-40%, 9.5 min) to obtain compound 2. MS ESI calculated for $C_{22}H_{26}N_4O_5S_3$ [M+H]$^+$ 523, found 523. $^1$H NMR (400 MHz, CD$_3$OD) δ ppm 8.04 (d, J=5.3 Hz, 1H), 7.41-7.43 (m, 2H), 7.17-7.19 (m, 1H), 6.85-6.87 (m, 2H), 6.75 (s, 1H), 6.40 (d, J=4.3 Hz, 1H), 3.94 (s, 3H), 3.13 (s, 6H), 3.04-3.13 (m, 1H), 1.21 (d, J=6.8 Hz, 6H).

Embodiment 3

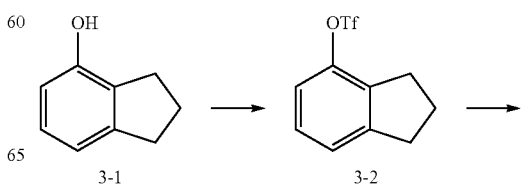

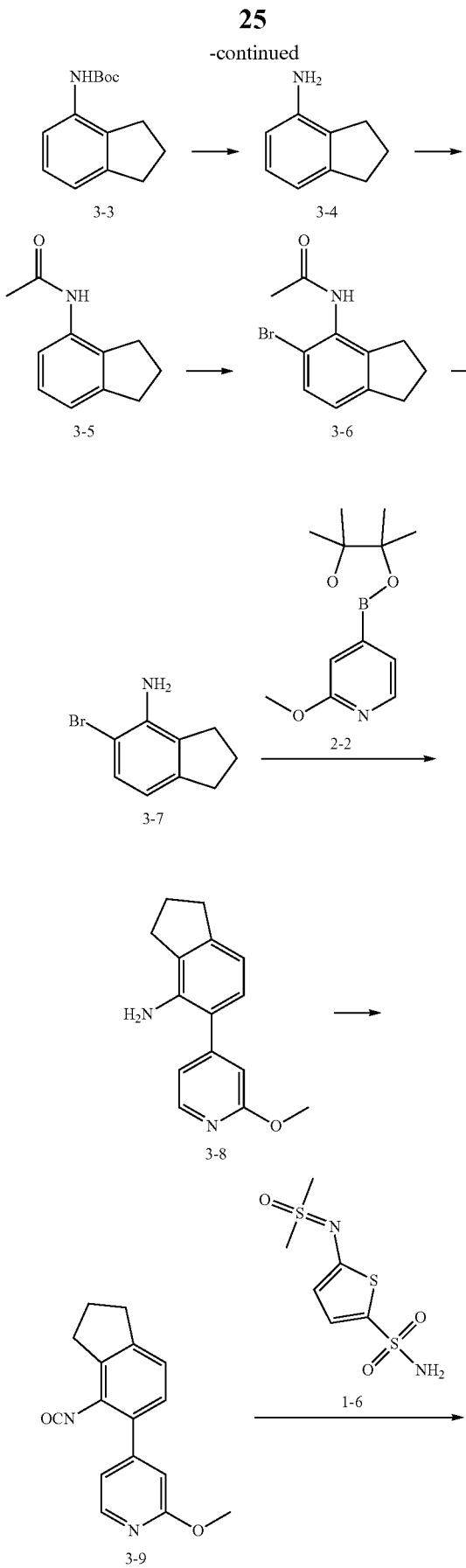

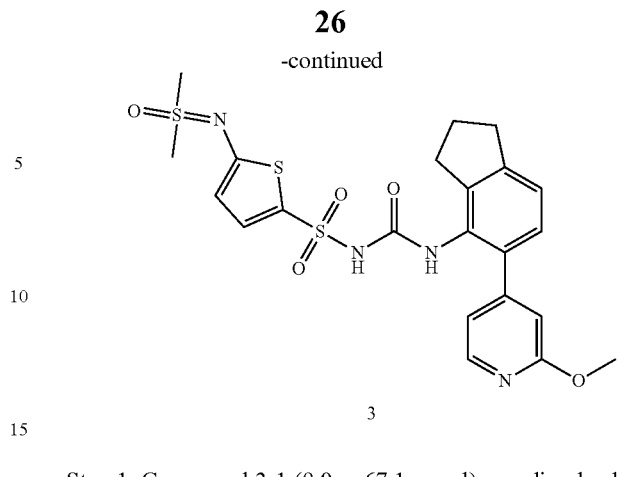

Step 1: Compound 3-1 (9.0 g, 67.1 mmol) was dissolved in dichloromethane (50 mL), and then trifluoromethane-sulfonic anhydride (37.8 g, 134.1 mmol) and pyridine (15.9 g, 201.23 mmol) were slowly added at 0° C., and the reaction was stirred at 25° C. for 1 hour, then quenched with water (50 mL) and extracted with dichloromethane (100 mL). The organic phase was concentrated, and the crude product was purified by column chromatography (petroleum ether:ethyl acetate=20:1) to obtain compound 3-2.

Step 2: Compound 3-2 (10.0 g, 37.5 mmol) and tert-butyl carbamate (8.8 g, 75.1 mmol) were dissolved in dioxane (150 mL), and then cesium carbonate (24.48 g, 75.12 mmol), 4,5-bis(diphenylphosphino)-9,9-dimethylxanthene (4.3 g, 7.5 mmol) and tris(dibenzylideneacetone)dipalladium (3.4 g, 3.7 mmol) were added under the protection of nitrogen, and the reaction was stirred at 80° C. for 1 hour. The reaction was quenched with water (50 mL) after the reaction was completed, extracted with ethyl acetate (150 mL). The organic phase was concentrated, and the crude product was purified by column chromatography (petroleum ether:ethyl acetate=5:1) to obtain compound 3-3. MS ESI calculated for $C_{14}H_{19}NO_2$ [M+H]$^+$ 234, found 234.

Step 3: Compound 3-3 (6.0 g, 25.7 mmol) was dissolved in dichloromethane (50 mL), and trifluoroacetic acid (17.6 g, 154.3 mmol) was added dropwise at 25° C., and the reaction was stirred at 25° C. for 1 hour, then quenched with saturated sodium bicarbonate (200 mL), extracted with dichloromethane (200 mL). The organic phase was concentrated to obtain compound 3-4, which was directly used in the next step. MS ESI calculated for $C_9H_{11}N$ [M+H]$^+$ 134, found 134.

Step 4: Compound 3-4 (2.6 g, 19.5 mmol) and triethylamine (2.6 g, 25.4 mmol) were dissolved in dichloromethane (30 mL), then acetic anhydride (2.3 g, 22.5 mmol) was added dropwise, and the reaction was stirred at 25° C. for 16 hours. The reaction was quenched with water (50 mL) after the reaction was completed, then extracted with dichloromethane (150 mL). The organic phase was concentrated, and the crude product was purified by column chromatography (petroleum ether:ethyl acetate=2:1) to obtain compound 3-5. MS ESI calculated for $C_{11}H_{13}NO$ [M+H]$^+$ 176, found 176.

Step 5: Compound 3-5 (2.9 g, 16.5 mmol) was dissolved in tetrahydrofuran (50 mL), and then p-toluenesulfonic acid (1.6 g, 9.1 mmol) and palladium acetate (185.7 mg, 827.5 μmol) were added, and N-bromosuccinimide (3.2 g, 18.2 mmol) was added after the reaction was stirred at 20° C. for 0.5 hours, and the reaction was continued to stir at 20° C. for 2 hours. The reaction was quenched with water (50 mL) after the reaction was completed, extracted with ethyl acetate (150 mL). After the organic phase was dried over anhydrous sodium sulfate, the organic phase was concentrated, and the crude product was purified by column chromatography (petroleum ether:ethyl acetate=2:1) to obtain compound 3-6. MS ESI calculated for $C_{11}H_{12}BrNO$ [M, M+2]$^+$ 254, 256, found 254, 256.

Step 6: Compound 3-6 (2.3 g, 9.1 mmol) was dissolved in ethanol (20 mL) and concentrated hydrochloric acid (7 mL, concentration of 37%), and the reaction was stirred at 80° C. for 12 hours. The reaction was quenched with saturated sodium bicarbonate (200 mL) after the reaction was completed, extracted with ethyl acetate (200 mL), and the organic phase was dried over anhydrous sodium sulfate and concentrated, and the crude product was separated by column chromatography (petroleum ether:ethyl acetate=2:1) to obtain compound 3-7. MS ESI calculated for $C_9H_{10}BrN$ [M, M+2]$^+$ 212, 214, found 212, 214.

Step 7: Compound 3-7 (200.0 mg, 943.0 μmol) and compound 2-2 (158.6 mg, 1.0 mmol) were dissolved in dioxane (16 mL)/water (4 mL), and then potassium carbonate (325.8 mg, 2.3 mmol) and [1,1'-bis(diphenylphosphino)ferrocene]dichloropalladium(II) (69.0 mg, 94.3 μmol) were added, and the reaction was stirred at 80° C. for 2 hours under the protection of nitrogen and then concentrated, and the crude product was purified by column chromatography (petroleum ether:ethyl acetate=1:1) to obtain compound 3-8. MS ESI calculated for $C_{15}H_{16}N_2O$ [M+H]$^+$ 241, found 241.

Step 8: Compound 3-8 (103.7 mg, 431.8 μmol) was dissolved in tetrahydrofuran (10 mL), and then triphosgene (55.1 mg, 185.6 μmol) and triethylamine (131.2 mg, 1.3 mmol) were added at 25° C., and the reaction was stirred at 25° C. for 0.5 hours. A solution of compound 3-9 in tetrahydrofuran was obtained by filtration after the reaction was completed, which was directly used in the next step. MS ESI calculated for $C_{16}H_{14}N_2O_2$ [M+H]$^+$ 267, found 267.

Step 9: Sodium hydride (39.3 mg, 982.9 mol, purity of 60%) was added to a solution of compound 1-6 (100.0 mg, 393.2 μmol) in tetrahydrofuran (10 mL), stirred at 0° C. for 10 min, and then a solution of compound 3-9 (104.7 mg, 393.2 μmol) in tetrahydrofuran (10 mL) was added to the system and stirred at 25° C. for 0.5 hours. The reaction was quenched with dilute hydrochloric acid (1 mol/L, 1 mL) after the reaction was completed, then extracted with ethyl acetate (50 mL×2). The organic phase was concentrated, and the crude product was separated by preparative high performance liquid chromatography (chromatographic column: Welch Xtimate C18 150*25 mm*5 μm; mobile phase: [water (10 mM ammonium bicarbonate)-acetonitrile]; acetonitrile %: 15%-40%, 9.5 min) to obtain compound 3. MS ESI calculated for $C_{22}H_{24}N_4O_5S_3$ [M+H]$^+$ 521, found 521. $^1$H NMR (400 MHz, CD$_3$OD) δ ppm 8.07 (d, J=5.3 Hz, 1H), 7.40-7.44 (m, 2H), 7.12-7.22 (m, 1H), 6.84 (d, J=4.3 Hz, 1H), 6.76 (s, 1H), 6.40 (d, J=4.3 Hz, 1H), 3.93 (s, 3H), 3.13 (s, 6H), 3.00 (t, J=7.4 Hz, 2H), 2.80-2.83 (m, 2H), 2.12 (t, J=7.4 Hz, 2H).

Embodiment 4

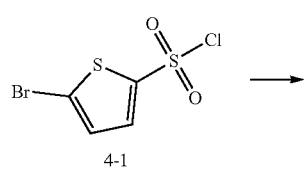

4-1

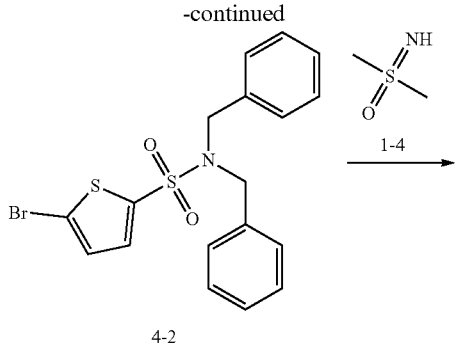

4-2

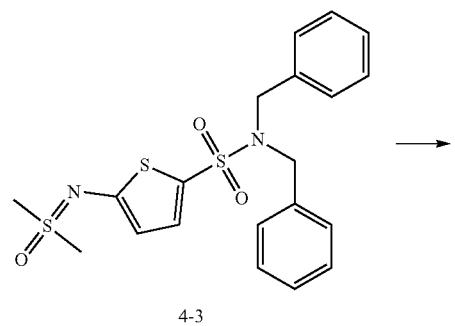

4-3

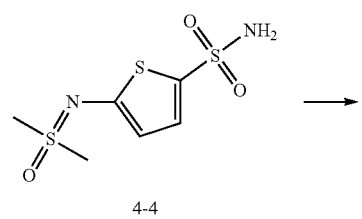

4-4

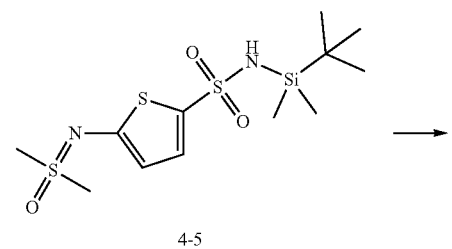

4-5

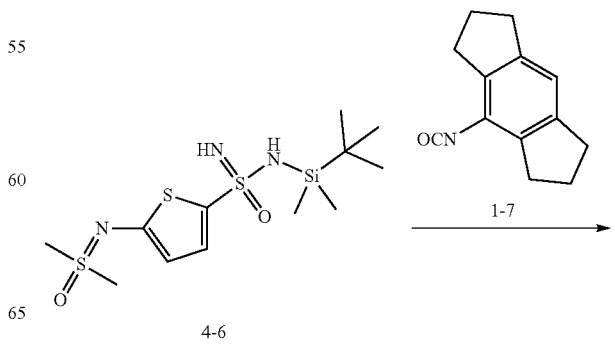

4-6

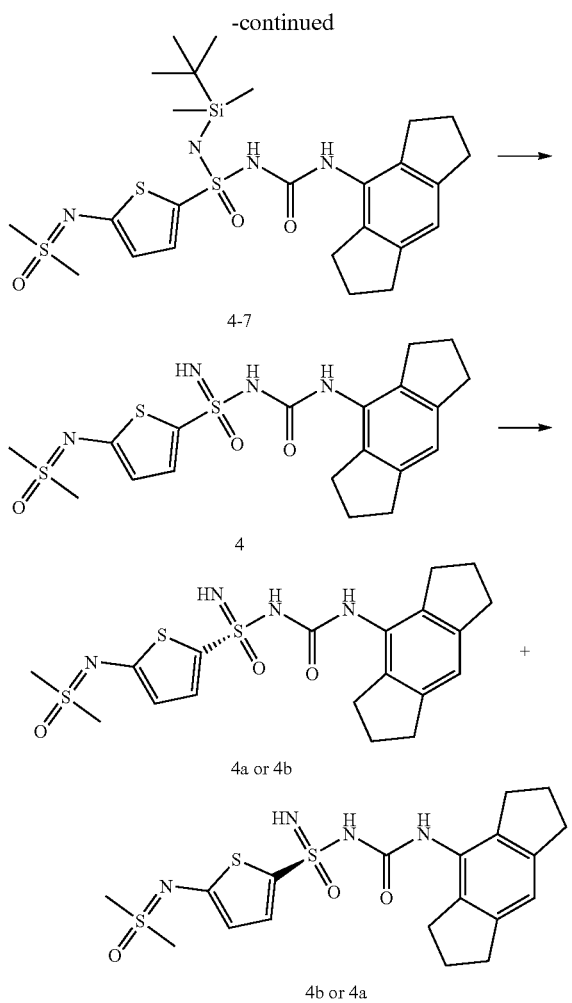

4-7

4

4a or 4b 4b or 4a

Step 1: Dibenzylamine (4.0 g, 20.1 mmol) and triethylamine (2.3 g, 22.9 mmol) were added slowly to a solution of compound 4-1 (5.0 g, 19.1 mmol) in dichloromethane (25 mL) in turn at 0° C., and the reaction was stirred at 25° C. for 12 hours. The reaction mixture was added to water (25 mL), extracted with dichloromethane (50 mL*3), and the organic phase was washed with saturated brine (25 mL), dried over anhydrous sodium sulfate, filtered, concentrated under reduced pressure and purified by column chromatography (petroleum ether: ethyl acetate=20:1-1:1) to obtain compound 4-2, which was directly used in the next step. MS ESI calculated for $C_{18}H_{16}BrNO_2S_2$ [M+H; M+H+2]$^+$ 422; 424, found 422; 424.

Step 2: Compound 4-2 (3.4 g, 8.1 mmol) was dissolved in 1,4-dioxane (40 mL), and then compound 1-4 (824.8 mg, 8.9 mmol), tris(dibenzylideneacetone)dipalladium (737.2 mg, 805.0 mol), 4,5-bis(diphenylphosphino)-9,9-dimethylxanthene (931.5 mg, 1.6 mmol) and cesium carbonate (5.3 g, 16.1 mmol) were added in turn, and the system was replaced with nitrogen for three times. The reaction was stirred at 110° C. for 12 hours and then cooled to 25° C. and filtered, and the filtrate was concentrated and purified by column chromatography (petroleum ether:ethyl acetate=10:1-0:1) to obtain compound 4-3, which was directly used in the next step. MS ESI calculated for $C_{20}H_{22}N_2O_3S_3$ [M+H]$^+$ 435, found 435.

Step 3: Concentrated sulfuric acid (5.4 g, 54.0 mmol, concentration of 98%) was added to a solution of compound 4-3 (2.4 g, 5.4 mmol) in dichloromethane (20 mL) at 0° C., and the reaction was stirred at 20° C. for 2 hours. About 30 g of ice was added to the reaction mixture, and the pH was adjusted to 5-6 with sodium hydroxide solid and then the mixture was extracted with a mixed solution of dichloromethane:methanol=10:1 (30 mL*3). The organic phase was dried over anhydrous sodium sulfate, concentrated and purified by column chromatography (dichloromethane:methanol=30:1-10:1) to obtain compound 4-4, which was directly used in the next step. MS ESI calculated for $C_6H_{10}N_2O_3S_3$ [M+H]$^+$ 255, found 255.

Step 4: A solution of compound 4-4 (1.0 g, 3.9 mmol) in tetrahydrofuran (20 mL) was cooled to 0° C., and sodium hydride (346.0 mg, 8.7 mmol, purity of 60%) was added, and then stirred for 0.5 hours. tert-Butyldimethylsilyl chloride (711.1 mg, 4.7 mmol) was added and warmed up to 25° C. and stirred for 12 hours. The reaction was cooled to 0° C., quenched with saturated aqueous ammonium chloride solution (10 mL), extracted with ethyl acetate (20 mL*3). The organic phase was washed with saturated brine (20 mL), dried over anhydrous sodium sulfate, concentrated under reduced pressure, purified by column chromatography (petroleum ether:ethyl acetate=3:1-0:1) to compound 4-5, which was directly used in the next step. MS ESI calculated for $C_{12}H_{24}N_2O_3S_3Si$ [M+H]$^+$ 369, found 369.

Step 5: Dichlorotriphenylphosphorane (2.0 g, 6.1 mmol) was dissolved in chloroform (20 mL), and triethylamine (1.1 g, 10.8 mmol) was added at 0° C., stirred for 15 min, then compound 4-5 (1.0 g, 2.7 mmol) was added, stirred at 0° C. for 0.5 hours, and then added to a saturated ammonia tetrahydrofuran solution (20 mL) which was precooled to −40° C., naturally warmed up to 25° C. and stirred for 12 hours. After the reaction was completed, the mixture was concentrated directly, and the residue was purified by preparative high performance liquid chromatography (chromatographic column: Welch Xtimate C18 250*70 mm: 10 μm; mobile phase: [water (10 mM ammonium bicarbonate)-acetonitrile]; acetonitrile %: 30%-57%, 30 min) to obtain compound 4-6, which was directly used in the next step. MS ESI calculated for $C_{12}H_{25}N_3O_2S_3Si$ [M+H]$^+$ 368, found 368.

Step 6: Compound 4-6 (150.0 mg, 408.0 μmol) was dissolved in tetrahydrofuran (10 mL), and sodium hydride (32.6 mg, 816.1 mol, purity of 60%) was added at 0° C. and stirred for 0.5 hours, then a solution of compound 1-7 (81.3 mg, 408.0 μmol) in tetrahydrofuran (10 mL) was added and the reaction was continued to stir at 25° C. for 1 hour. The reaction mixture was cooled to 0° C. and quenched with water (2 mL) to obtain a solution of compound 4-7, which was directly used in the next step. MS ESI calculated for $C_{25}H_{38}N_4O_3S_3Si$ [M+H]$^+$ 567, found 567.

Step 7: Dilute hydrochloric acid (1 mol/L, 10 mL) was added to the solution of compound 4-7 and stirred at 25° C. for 0.5 hours. The mixture was concentrated under reduced pressure to remove the solvent, and the residue was purified by preparative high performance liquid chromatography (chromatographic column: Welch Xtimate C18 250*70 mm #10 μm; mobile phase: [water (10 mM ammonium bicarbonate)-acetonitrile]; acetonitrile %: 27%-47%, 25 min) to obtain compound 4. MS ESI calculated for $C_{19}H_{24}N_4O_3S_3$ [M+H]$^+$ 453, found 453.

Step 8: Compound 4 (100 mg) was separated by preparative supercritical fluid chromatography (chromatographic column: Chiralcel OD-3 100 mm*4.6 mm I.D., 3 μm); mobile phase: [A: carbon dioxide, B: methanol (0.05% diethylamine)], gradient: B %: 5%-40%, 4 min; B %: 40%, 2.5 min; B %: 5%, 1.5 min) to obtain compound 4a (retention time was 4.68 min) and compound 4b (retention time was 5.24 min).

Compound 4a, $^1$H NMR (400 MHz, DMSO-d$_6$) δ=8.26 (s, 1H), 7.47 (s, 2H), 7.29 (d, J=4.0 Hz, 1H), 6.86 (s, 1H), 6.28 (d, J=4.0 Hz, 1H), 3.29 (s, 6H), 2.78 (t, J=7.4 Hz, 4H), 2.69 (t, J=7.4 Hz, 4H), 1.93 (t, J=7.4 Hz, 4H). MS ESI calculated for C$_{19}$H$_{24}$N$_4$O$_3$S$_3$ [M+H]$^+$ 453, found 453.

Compound 4b, $^1$H NMR (400 MHz, DMSO-d$_6$) δ=8.30 (s, 1H), 7.49 (s, 2H), 7.30 (d, J=4.0 Hz, 1H), 6.88 (s, 1H), 6.30 (d, J=4.0 Hz, 1H), 3.32 (s, 6H), 2.79 (t, J=7.4 Hz, 4H), 2.71 (t, J=7.4 Hz, 4H), 1.94 (t, J=7.4 Hz, 4H). MS ESI calculated for C$_{19}$H$_{24}$N$_4$O$_3$S$_3$ [M+H]$^+$ 453, found 453.

Embodiment 5 directly used in the next step. MS ESI calculated for C$_{28}$H$_{39}$N$_5$O$_4$S$_3$Si [M+H]$^+$ 634, found 634.

Step 2: Concentrated hydrochloric acid (5.0 mL, concentration of 37%) was added dropwise to the reaction mixture of compound 5-1 at 0° C. and stirred for 10 min, extracted with ethyl acetate (30 mL) after the reaction was completed. The organic phase was dried over anhydrous sodium sulfate. The obtained crude product was separated by column chromatography (dichloromethane:methanol=10:1) to obtain compound 5. MS ESI calculated for C$_{22}$H$_{25}$N$_5$O$_4$S$_3$ [M+H]$^+$ 520, found 520.

Step 3: Compound 5 (90 mg) was separated by preparative chromatography (chromatographic column: Cellulose-2 100 mm*4.6 mm I.D., 3 μm; mobile phase A: carbon dioxide; B: [0.05% diethylamine-methanol]; gradient: B %:

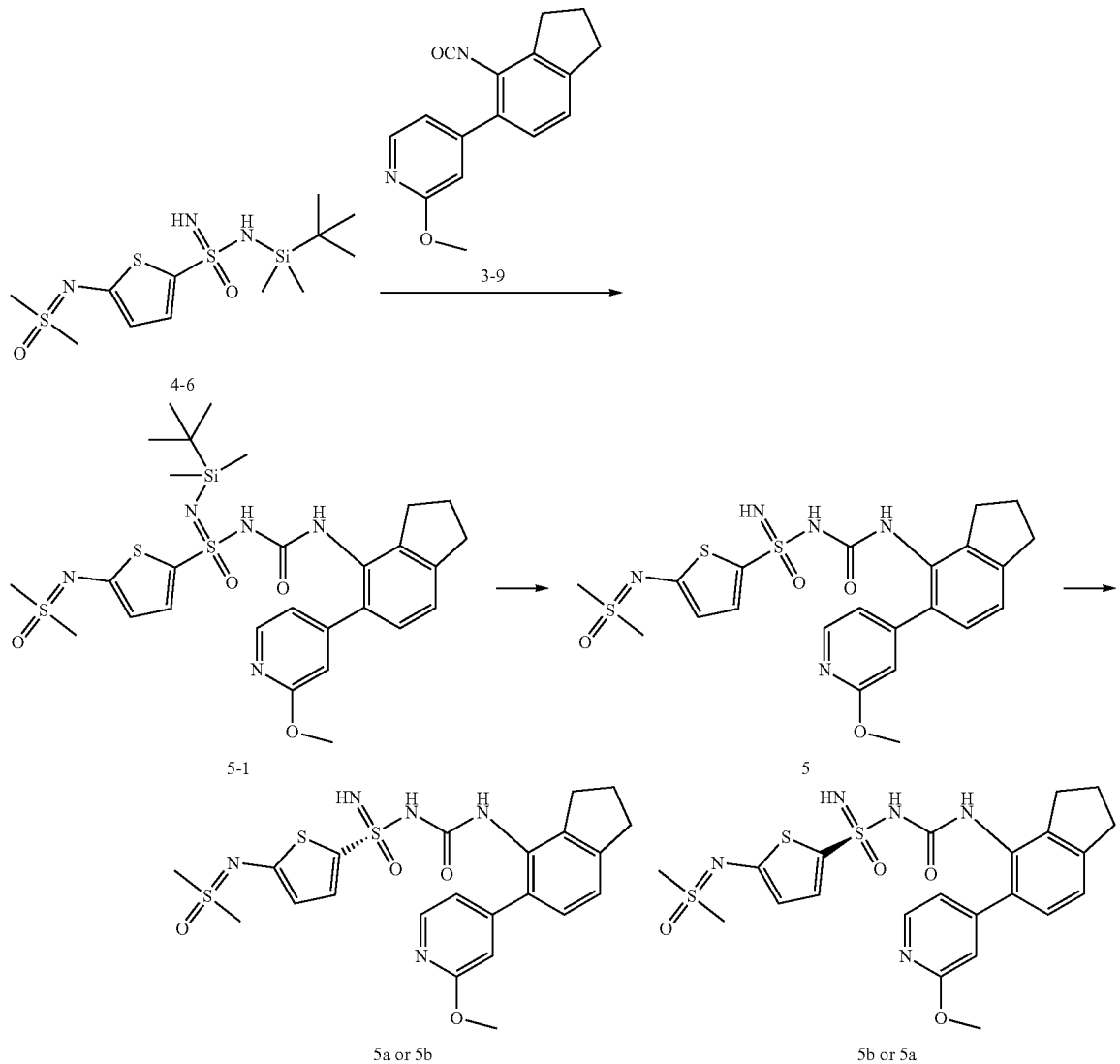

Step 1: Sodium hydride (43.5 mg, 1.1 mmol, purity of 60%) was added to a solution of compound 4-6 (100.0 mg, 272.0 μmol) in tetrahydrofuran (10.0 mL), stirred at 25° C. for 0.5 hours, and then compound 3-9 (72.4 mg, 272.0 μmol) was added to the system and continued to stir for 1 hour to obtain a reaction mixture of compound 5-1, which was 50%-50%, 25 min) to obtain compound 5a (retention time was 2.58 min) and compound 5b (retention time was 3.82 min).

Compound 5a, $^1$H NMR (400 MHz, DMSO-d$_6$) δ ppm 8.26 (brs, 1H), 8.12 (d, J=5.3 Hz, 1H), 7.42 (brs, 2H), 7.15-7.25 (m, 1H), 7.06-7.14 (m, 2H), 6.95 (brd, J=4.8 Hz, 1H), 6.76 (s, 1H), 6.25 (d, J=4.0 Hz, 1H), 3.88 (s, 3H), 3.32 (s, 6H), 2.92 (t, J=7.4 Hz, 2H), 2.79 (brs, 2H), 1.96-2.03 (m, 2H). MS ESI calculated for $C_{22}H_{25}N_5O_4S_3$ [M+H]$^+$ 520, found 520.

Compound 5b, $^1$H NMR (400 MHz, DMSO-d$_6$) δ ppm 8.26 (brs, 1H), 8.12 (d, J=5.3 Hz, 1H), 7.42 (brs, 2H), 7.15-7.21 (m, 1H), 7.06-7.16 (m, 2H), 6.95 (brd, J=4.8 Hz, 1H), 6.76 (s, 1H), 6.25 (d, J=4.0 Hz, 1H), 3.88 (s, 3H), 3.32 (s, 6H), 2.92 (brt, J=7.4 Hz, 2H), 2.79 (brs, 2H), 1.98-2.03 (m, 2H). MS ESI calculated for $C_{22}H_{25}N_5O_4S_3$ [M+H]$^+$ 520, found 520.

Embodiment 6

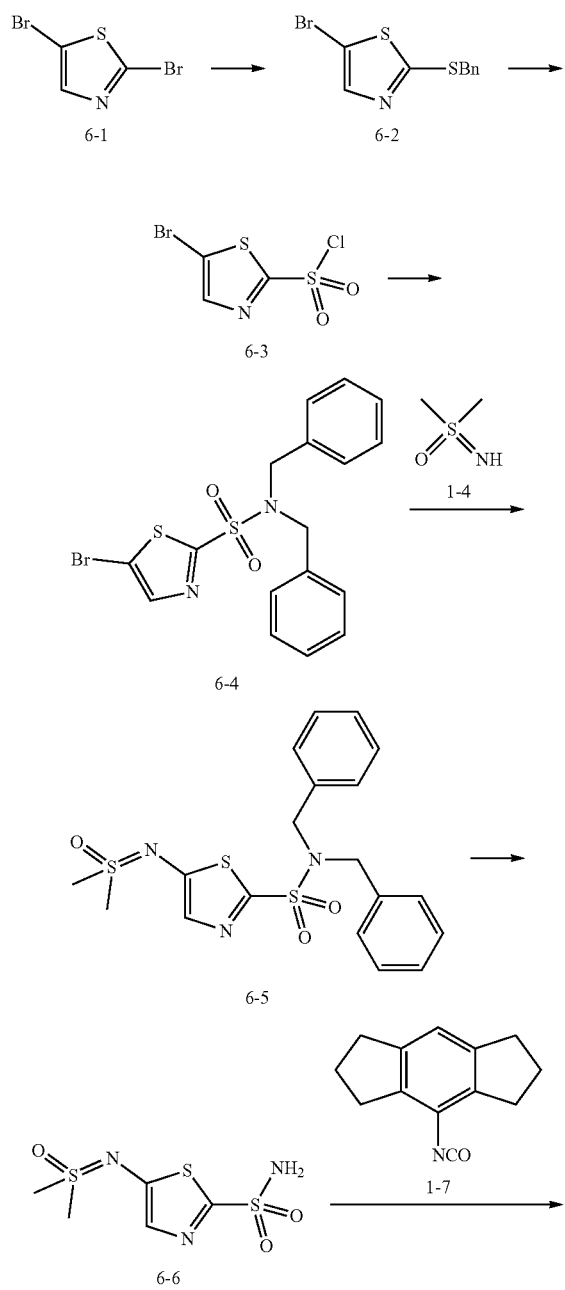

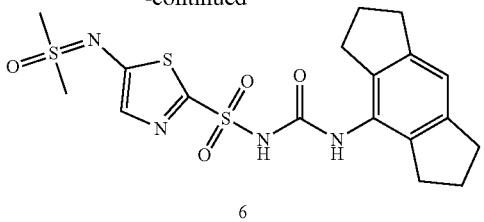

6

Step 1: Potassium carbonate (5.1 g, 37.0 mmol) was added to a solution of benzyl mercaptan (1.5 g, 12.3 mmol) in N,N-dimethylformamide (30 mL), stirred at 25° C. for 5 min, and then compound 6-1 (3.0 g, 12.4 mmol) was added. The reaction was warmed up to 100° C. and continued to stir for 5 hours, quenched with water (60 mL), extracted with ethyl acetate (60 mL*3). The combined organic phases were washed with saturated brine (200 mL), dried over anhydrous sodium sulfate, filtered, and concentrated under reduced pressure to obtain compound 6-2, which was directly used in the next step. $^1$H NMR (400 MHz, CDCl$_3$): 7.51 (s, 1H), 7.20-7.33 (m, 5H), 4.35 (s, 2H). MS ESI calculated for $C_{10}H_8BrNS_2$ [M+H; M+H+2]$^+$ 286; 288, found 286; 288.

Step 2: Compound 6-2 (1.0 g, 3.5 mmol), acetic acid (10 mL), water (5 mL) and 1,3-dichloro-5,5-dimethylhydantoin (2.8 g, 14.0 mmol) were added to a pre-dried reaction flask and the reaction was stirred at 40° C. for 1.5 hours. The reaction mixture was quenched with water (20 mL) after the reaction was completed, extracted with dichloromethane (20 mL*3). The combined organic phases were washed with saturated brine (30 mL), dried over anhydrous sodium sulfate, filtered, and the filtrate was concentrated under reduced pressure. Petroleum ether (1 mL) and ethyl acetate (1 mL) were added to the residue, stirred for 10 minutes and then filtered, and the filtrate was concentrated under reduced pressure to obtain compound 6-3, which was immediately used in the next step.

Step 3: Compound 6-3 (800.0 mg, 3.1 mmol) was dissolved in 1,2-dichloroethane (10 mL), and dibenzylamine (2.4 g, 12.2 mmol) was added. The reaction was stirred at 80° C. for 12 hours and then cooled to 25° C., quenched by adding water (40 mL) to the reaction mixture, extracted with ethyl acetate (40 mL*3), and the combined organic phases were washed with saturated brine (100 mL), dried over anhydrous sodium sulfate, filtered and concentrated under reduced pressure. The residue was purified by column chromatography (dichloromethane:methanol=20:1) to obtain compound 6-4. MS ESI calculated for $C_{17}H_{15}BrN_2O_2S_2$ [M+H; M+H+2]$^+$ 423; 425, found 423; 425.

Step 4: Compound 6-4 (390.0 mg, 992.1 mol), 1,4-dioxane (10 mL), compound 1-4 (138.6 mg, 1.5 mmol) and cesium carbonate (969.7 mg, 2.9 mmol) were added to a pre-dried reaction flask, and 4,5-bis(diphenylphosphino)-9,9-dimethylxanthene (114.8 mg, 198.4 μmol) and tris(dibenzylideneacetone)dipalladium (90.8 mg, 99.2 μmol) were added finally. The reaction was stirred at 110° C. for 2 hours under the protection of nitrogen and then cooled to 25° C., quenched by adding water (20 mL) to the reaction mixture, extracted with ethyl acetate (20 mL*3), and the combined organic phases were washed with saturated brine (20 mL*3), dried over anhydrous sodium sulfate, filtered and concentrated under reduced pressure. The residue was purified by column chromatography (dichloromethane:methanol=10:1) to obtain compound 6-5. MS ESI calculated for $C_{19}H_{21}N_3O_3S_3$ [M+H]$^+$ 436, found 436.

Step 5: Compound 6-5 (150 mg, 344.3 μmol) was dissolved in dichloromethane (1 mL), and concentrated sulfuric acid (1 mL, concentration of 98%) was added. The reaction was stirred at 25° C. for 0.5 hours. The reaction mixture was slowly poured into ice water (5 mL) after the reaction was completed, and the pH was adjusted to 4-5 with 2 mol/L sodium hydroxide solution, and concentrated under reduced pressure to obtain a residue, and the residue was separated by column chromatography (dichloromethane:methanol=20:1) to obtain compound 6-6. MS ESI calculated for $C_5H_9N_3O_3S_3$ [M+H]$^+$ 256, found 256.

Step 6: Compound 6-6 (220.0 mg, 86.1 μmol) was dissolved in tetrahydrofuran (1 mL), and sodium hydride (10.3 mg, 258.4 mol, purity of 60%) was added at 0° C. and stirred for 0.5 hours, then compound 1-7 (20.6 mg, 103.3 μmol) was added. The reaction was warmed up to 25° C. and continued to stir for 0.5 hours, quenched with water (0.5 mL) and concentrated under reduced pressure, and the residue was purified by preparative thin-layer chromatography (dichloromethane:methanol=10:1) to obtain compound 6. $^1$H NMR (400 MHz, CD$_3$OD) δ ppm 7.10 (brs, 1H), 6.89 (s, 1H), 3.27 (s, 6H), 2.82 (t, J=7.1 Hz, 4H), 2.69-2.76 (m, 4H), 1.96-2.03 (m, 4H); MS ESI calculated for $C_{18}H_{22}N_4O_4S_3$ [M+H]$^+$ 455, found 455.

Embodiment 7

Step 1: Compound 6-6 (200.0 mg, 783.3 μmol) was dissolved in tetrahydrofuran (20 mL), and sodium hydride (78.3 mg, 1.9 mmol, purity of 60%) was added at 0° C. and stirred for 0.5 hours, then tert-butyldimethylsilyl chloride (141.6 mg, 939.9 μmol) was added and stirred at 25° C. for 1 hour, quenched with saturated ammonium chloride solution (5 mL) after the reaction was completed, and extracted with ethyl acetate (30 mL*2). The combined organic phases were dried over anhydrous sodium sulfate, concentrated and the residue was separated by column chromatography (dichloromethane:methanol=20:1) to obtain compound 7-1. MS ESI calculated for $C_{11}H_{23}N_3O_3S_3Si$ [M+H]$^+$ 370, found 370.

Step 2: Triethylamine (260.7 mg, 2.5 mmol) was added dropwise to a solution of dichlorotriphenylphosphorane (429.3 mg, 1.3 mmol) in chloroform (10 mL) at 25° C., stirred for 10 min and then cooled to 0° C. A solution of compound 7-1 (190.0 mg, 515.5 μmol) in chloroform (3 mL) was added and the reaction was continued to stir at 0° C. for 0.5 hours. Ammonia was introduced into the system for 15 min, then the reaction was warmed up to 25° C. and stirred for 1 hour. After the reaction was completed, the mixture was concentrated to obtain compound 7-2, which was directly used in the next step. MS ESI calculated for $C_{11}H_{24}N_4O_2S_3Si$ [M+H]$^+$ 369, found 369.

Step 3: Sodium hydride (78.13 mg, 1.95 mmol, purity of 60%) was added to a solution of compound 7-2 (180.0 mg,

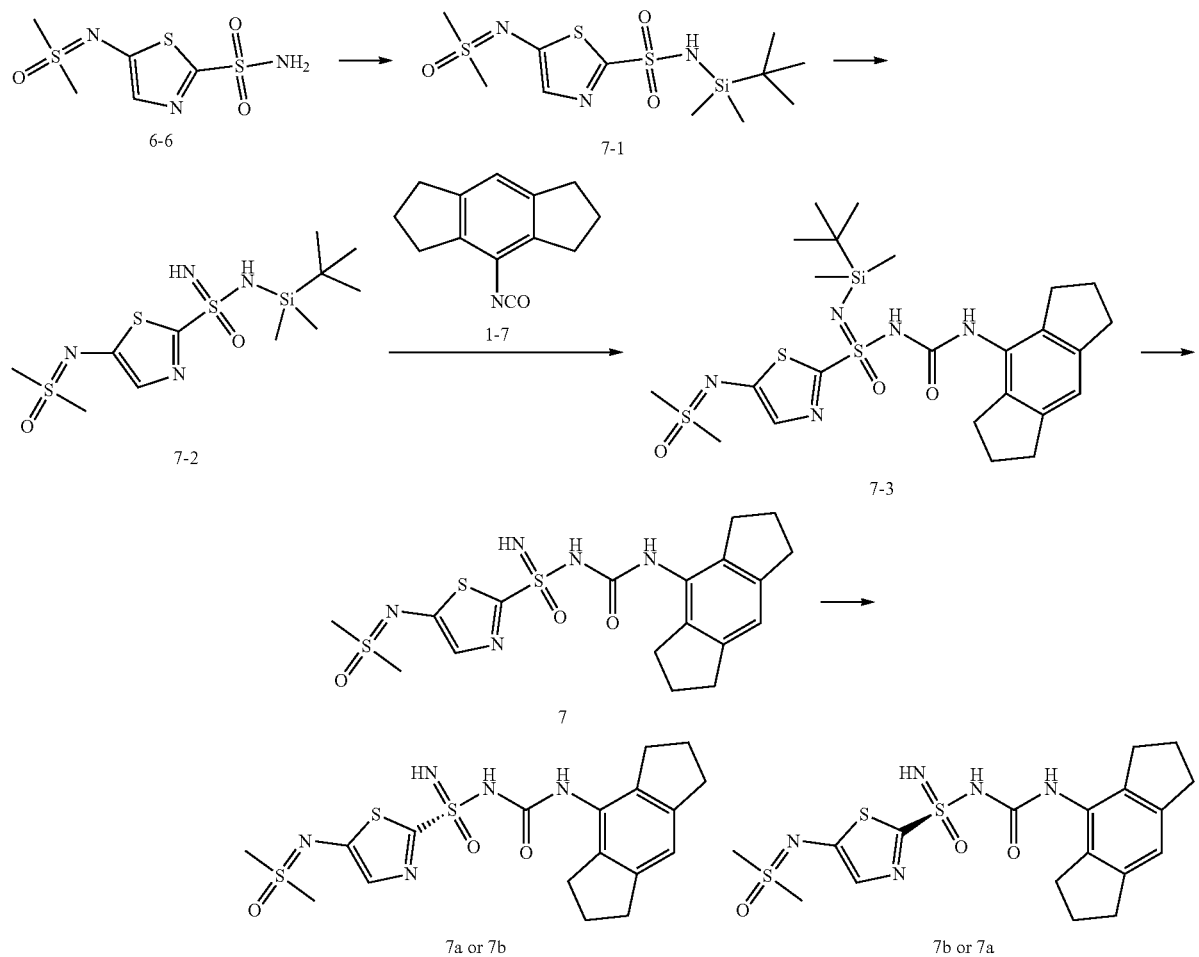

488.32 μmol) in tetrahydrofuran (20 mL), stirred at 25° C. for 0.5 hours, and then compound 1-7 (97.3 mg, 488.3 μmol) was added to the system and continued to stir for 1 hour. After the reaction was completed, the reaction mixture of compound 7-3 was directly used in the next step. MS ESI calculated for $C_{24}H_{37}N_5O_3S_3Si$ [M+H]$^+$ 568, found 568.

Step 4: Concentrated hydrochloric acid (5.0 mL, concentration of 37%) was added dropwise to the reaction mixture of compound 7-3 at 0° C. and stirred for 10 min, extracted with ethyl acetate (30 mL) after the reaction was completed, and the organic phase was dried over anhydrous sodium sulfate. The obtained crude product was separated by column chromatography (dichloromethane:methanol=10:1) to obtain compound 7. MS ESI calculated for $C_{18}H_{23}N_5O_3S_3$ [M+H]$^+$ 454, found 454.

Step 5: Compound 7 (20 mg) was separated by preparative supercritical fluid chromatography (chromatographic column: Chiralpak AS-3 150 mm*4.6 mm I.D., 3 μm); mobile phase: [A: carbon dioxide, B: ethanol (0.05% diethylamine)]; gradient: B %: 5%-40%, 5 min; B %: 40%, 2.5 min; B %: 5%, 2.5 min) to obtain compound 7a (retention time was 5.53 min) and 7b (retention time was 6.15 min).

Compound 7a: $^1$H NMR (400 MHz, DMSO-d$_6$) δ ppm 8.41 (brs, 1H), 7.73 (brs, 2H), 7.23 (s, 1H), 6.87 (s, 1H), 3.35 (s, 6H), 2.78 (brt, J=7.3 Hz, 4H), 2.67 (brs, 4H), 1.86-1.97 (m, 4H). MS ESI calculated for $C_{18}H_{23}N_5O_3S_3$ [M+H]$^+$ 454, found 454.

Compound 7b: $^1$H NMR (400 MHz, DMSO-d$_6$) δ ppm 8.42 (brs, 1H), 7.73 (brs, 2H), 7.23 (s, 1H), 6.87 (s, 1H), 3.35 (brs, 6H), 2.78 (brt, J=7.0 Hz, 4H), 2.68 (brs, 4H), 1.93 (brt, J=7.3 Hz, 4H). MS ESI calculated for $C_{18}H_{23}N_5O_3S_3$ [M+H]$^+$ 454, found 454.

Embodiment 8

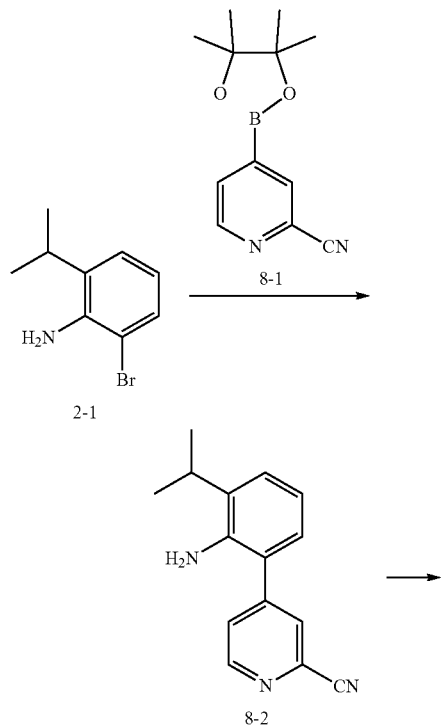

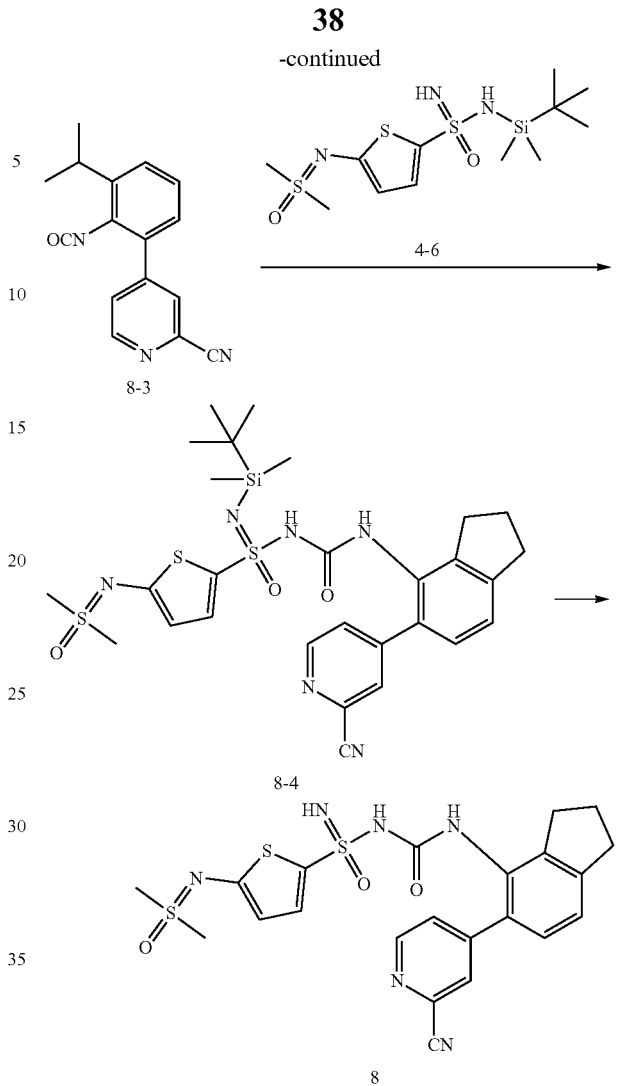

Step 1: Compound 2-1 (2.0 g, 9.3 mmol) and compound 8-1 (2.2 g, 9.3 mmol) were dissolved in dioxane (40 mL)/water (8 mL), and then [1,1'-bis(diphenylphosphino)ferrocene]dichloropalladium(II) dichloromethane complex (762.8 mg, 934.1 μmol) and potassium carbonate (2.6 g, 18.6 mmol) were added, and the reaction was stirred at 100° C. for 2 hours then cooled to 25° C., extracted with water (50 mL) and ethyl acetate (150 mL). The organic phase was dried over anhydrous sodium sulfate and concentrated, and the crude product was purified by column chromatography (petroleum ether:ethyl acetate=2:1) to obtain compound 8-2. MS ESI calculated for $C_{15}H_{15}N_3$ [M+H]$^+$ 238, found 238.

Step 2: Compound 8-2 (1.0 g, 4.2 mmol) was dissolved in tetrahydrofuran (60 mL), and then triphosgene (537.7 mg, 1.8 mmol) and triethylamine (1.3 g, 12.6 mmol) were added at 25° C., and the reaction was stirred at 25° C. for 0.5 hours. After the reaction was completed, the reaction mixture was filtered to obtain a reaction mixture of compound 8-3 in tetrahydrofuran, which was directly used in the next step. MS ESI calculated for $C_{16}H_{13}N_3O$ [M+H]$^+$ 264, found 264.

Step 3: Sodium hydride (43.5 mg, 1.1 mmol, purity of 60%) was added to the reaction mixture of compound 4-6 (100.0 mg, 272.0 μmol) in tetrahydrofuran (10.0 mL) at 25° C. and stirred for 0.5 hours, then compound 8-3 (71.1 mg, 272.0 μmol) was added to the system and continued to stir for 1 hour. After the reaction was completed, the reaction mixture of compound 8-4 was directly used in the next step. MS ESI calculated for $C_{28}H_{36}N_6O_3S_3Si$ [M+H]$^+$ 629, found 629.

Step 4: Concentrated hydrochloric acid (5 mL, concentration of 37%) was added dropwise to the reaction mixture of compound 8-4 at 0° C. and stirred for 10 min, extracted with ethyl acetate (30 mL) after the reaction was completed. The organic phase was dried over anhydrous sodium sulfate, filtered, and the crude product was concentrated and separated by column chromatography (dichloromethane:methanol=20:1) to obtain compound 8. $^1$H NMR (400 MHz, CD$_3$OD) δ ppm 8.67 (d, J=5.5 Hz, 1H), 7.90 (brs, 1H), 7.87-8.01 (m, 1H), 7.62-7.74 (m, 1H), 7.23-7.33 (m, 2H), 7.17-7.21 (m, 1H), 6.38 (d, J=4.5 Hz, 1H), 3.34-3.40 (s, 6H), 2.91-3.06 (m, 4H), 2.12 (brt, J=7.0 Hz, 2H). MS ESI calculated for $C_{22}H_{22}N_6O_3S_3$ [M+H]$^+$ 515, found 515.

Biological Test Data

Experimental Embodiment 1: IC$_{50}$ Experiment for the Detection of NLRP3 Antagonist Using THP-1 Cells The chemical names and structural formulas of the compounds of the present disclosure for experimental use are shown in the preparation embodiments for each compound.

1. Experimental principle: In this experiment, the human monocytic cell line THP1 was used to study the inhibitory activity (IC$_{50}$) of NLRP3 antagonists on the secretion of IL-1β. The monocytic cell line THP1 was differentiated into mature macrophages using PMA (phorbol 12-myristate 13-acetate), and then the cells were stimulated using LPS (lipopolysaccharide), an agonist of Toll-like receptor TLR4, to activate the transcriptional activity of inflammasome NLRP3 and the expression of IL-1β precursor pro-IL-1β. At this time, the NLRP3 antagonist was added, and then ATP was added to further mature and activate NLRP3, and activate downstream caspase-1. Pro-IL-1β could be enzyme-cleaved by the activated caspase-1 to mature IL-1β that could be secreted. The NLRP3 antagonist could effectively inhibit the maturation and activation of NLRP3 induced by ATP, as well as the activation of downstream caspase-1, thereby inhibiting the maturation and secretion of IL-1β.

2. Experimental materials:

2.1 Reagents are shown in Table 1:

TABLE 1

| Name | Supplier | Item number or serial number | Storage condition |
|---|---|---|---|
| PMA | Sigma | 79346 | −20° C. |
| LPS | InvivoGen | tlrl-eblps | −20° C. |
| ATP | — | — | −20° C. |
| 1640 medium | Gibco | 22400-089 | 4° C. |
| FBS | HyClone | SV30087.03 | −80° C. |
| Penicillin-streptomycin | HyClone | SV30010 | 4° C. |
| β-Mercaptoethanol | Sigma | M3148 | Room temperature |
| NEAA non-essential amino acids | Gibco | 1140-050 | 4° C. |
| Human soluble protein kit | BD | 558265 | Room temperature |
| Human IL-1β Flex Set | BD | 558279 | Room temperature |
| 96-well flat-bottom plate | Corning | 3599 | Room temperature |
| 96-well U-bottom plate | Corning | 3799 | Room temperature |

2.2 Instruments are shown in Table 2:

TABLE 2

| Name | Supplier | Item number or serial number |
|---|---|---|
| Flow Cytometer | BD | LSRFortessa |

2.3 Experimental steps:

(1) The density of THP1 cells was adjusted to 5*10$^5$ cells/mL, then PMA was added, and the final concentration was adjusted to 100 ng/mL, and the cells were inoculated into a 96-well flat-bottom plate with 200 μL/well, stimulated overnight at 37° C. and 5% CO$_2$ (<16 hours if possible).

(2) The next day, the supernatant was discarded, and then carefully washed twice with Dulbecco's phosphate buffer (200 μL/time).

(3) The cells were stimulated with LPS, and the final concentration of LPS was 100 ng/mL, added to a 96-well plate with 200 μL/well, and cultured at 37° C. and 5% CO$_2$ for 3 hours.

(4) The test compounds were added to the wells and the screening concentrations were respectively: 5 μM, 1 μM, 200 nM, 40 nM, 8 nM, 1.6 nM, 0.32 nM and 0.064 nM. The cells were incubated at 37° C. and 5% CO$_2$ incubator for 1 hour.

(5) ATP was added to each well at a final concentration of 5 mM, and incubated overnight (>18 hours) at 37° C. and 5% CO$_2$.

(6) On the third day, 5 μL of the supernatant was taken out, diluted 10 times, and the content of IL-1β in the supernatant was detected by CBA.

3. Experimental results:

The activity results of compounds are shown in Table 3.

TABLE 3

Results of NLRP3 antagonist inhibitory activity for compounds

| Compound | IL-1β inhibitory activity in THP-1 cell IC$_{50}$ (nM) |
|---|---|
| 1 | 36.5 |
| 2 | 40.0 |
| 3 | 10.0 |
| 4a | 33.9 |
| 5a | 7.4 |
| 7a | 9.8 |
| 8 | 27.8 |

Experimental conclusion: The compounds of the present disclosure exhibits good NLRP3 inhibitory activity.

Experimental Embodiment 2: Pharmacokinetic Evaluation of Compounds

Experimental Objective: To Test the Pharmacokinetics of Compounds in Mice
Experimental Materials: C57BL/6J Mice (Male, 6-8 Weeks Old)

Experimental operation: The clear solution obtained after the test compound was dissolved was administered to female C57BL/6J mice (overnight fasting, 6-8 weeks old) via tail intravenous injection and intragastric administration (vehicle: 10% DMSO/10% solutol/80% water). After administration of test compound or control compound, blood was collected from the mandibular vein and centrifuged to obtain plasma at 0.0833, 0.25, 0.5, 1, 2, 4, 8 and 24 h for the intravenous injection group (IV) and at 0.25, 0.5, 1, 2, 4, 6, 8 and 24 h for the intragastric administration group (PO). The plasma concentration was determined by LC-MS/MS, and relevant pharmacokinetic parameters were calculated by the non-compartmental model linear logarithmic trapezoidal method using pharmacokinetic software WinNonlin™ Version 6.3. Meaning of each parameter: $T_{1/2}$: half-life; $C_{max}$: peak concentration; $AUC_{0-inf}$: area under the plasma concentration-time curve from time 0 extrapolated to infinite time; F: bioavailability, Vd: apparent volume of distribution, Cl: clearance rate, $T_{max}$: time to peak. The test results are shown in Table 4:

TABLE 4

Results of pharmacokinetic test of compound 7a

| Parameter | | Compound 7a |
|---|---|---|
| IV | $T_{1/2}$ (h) | 2.10 |
| 3 mg/kg | Vd (L/kg) | 0.25 |
| | Cl (mL/min/kg) | 1.68 |
| | $AUC_{0-inf}$ (nM*h) | 65725 |
| PO: | $C_{max}$ (nM) | 101913 |
| 20 mg/kg | $T_{max}$ (h) | 0.5 |
| | $AUC_{0-inf}$ (nM*h) | 296204 |
| | F (%) | 67.6 |

Conclusion: The compounds of the present disclosure have good oral bioavailability, high exposure, and good pharmacodynamic properties in vivo.

Experimental Embodiment 3: Evaluation of the Therapeutic Effect of the Compound on the MSU-Induced Air Pouch Acute Gout Model in C57BL/6 Mice Air Pouch of mouse is a cystic space similar to the human synovial membrane, and the injection of monosodium urate crystals (MSU) into the air pouch will cause an acute inflammatory response similar to human gout. The inflammatory cytokines IL-6 and IL-1β in the Air Pouch Lavage Fluid flushing fluid (APLV) were analyzed, and MCC950 was used as a control compound, and the efficacy of the compound of the present disclosure on the MSU-induced air pouch gout model in male C57BL/6 mice was tested.

Experimental objective: To evaluate the effect of the compound of the present disclosure on treating acute gout with Air Pouch gout model in mice.

Experimental animals: C57BL/6 mice, male, 7-8 weeks old, Beijing Vital River Laboratory Animal Technology Co., Ltd.

Experimental Design:

As shown in FIG. 1, experimental healthy mice were numbered and grouped, and sterile air was injected into the back of the mice on the first day (Day 1) and on the fourth day (Day 4) to generate air pouch. On the seventh day, the drug was administered first, and the MSU crystal solution was injected into the air pouch after 1 hour, and the Air Pouch Lavage Fluid (APLV) was collected after 7 hours and analyzed. Grouping and administration scheme are shown in Table 5.

TABLE 5

Grouping and administration scheme

| Group | Number of animals | Immunogen | Test drug | Administration dosage and pathway | Vehicle |
|---|---|---|---|---|---|
| 1 | 5 | None | Navie | — | — |
| 2 | 8 | MSU (3 mg) | Vehicle | — | — |
| 3 | 8 | MSU (3 mg) | MCC950 | 50 mg/kg; po | 10% DMSO/10% solutol/ 80% water |
| 4 | 8 | MSU (3 mg) | Embodiment 7a | 50 mg/kg; po | 10% DMSO/10% solutol/ 80% water |
| 5 | 8 | MSU (3 mg) | Embodiment 7a | 15 mg/kg; po, | 10% DMSO/10% solutol/ 80% water |
| 6 | 8 | MSU (3 mg) | Embodiment 7a | 5 mg/kg; po | 10% DMSO/10% solutol/ 80% water |
| 7 | 8 | MSU (3 mg) | Dex. | 10 mg/kg; ip | Physiological saline |

Note:
Navie: healthy control group;
Vehicle: vehicle control group;
MCC950: reference compound;
Dex.: dexamethasone;
po: oral administration;
ip: intraperitoneal injection.

Experimental Methods and Steps:
1.1 Preparation of MSU 1 g of uric acid was dissolved in 0.2 L of boiling water containing 6 mL of 1 N sodium hydroxide; after the pH was adjusted to 7.4, the solution was gradually cooled at room temperature and then left overnight at 4° C. MSU crystals were recovered by centrifugation and evaporated to dryness, dispensed into individual vials (3 mg), and sterilized by autoclaving.

1.2 Grouping, Administration and Detection of IL-6 and IL-1β

Healthy C57BL/6 mice were numbered and grouped in the experiment, and 5 mL of sterile air was subcutaneously injected into the back of the mice on the same day of grouping (Day 1) and on the fourth day (Day 4) to generate an air pouch. On the seventh day (Day 7), each group of mice was given vehicle or test sample, and after 1 hour the suspension of MSU crystals (saline, 3 mg/mL) was injected into the air pouch. Air Pouch Lavage Fluid (APLV) would be collected after 6 hours, and ELISA kits would be used to test the levels of IL-6 and IL-1β in APLV. Results were expressed as average value±SEM. Statistical analysis was performed by a method of analysis of variance (ANOVA), followed by Dunnett test, and differences were considered significant when p<0.05.

Experimental Results

Figure 2:
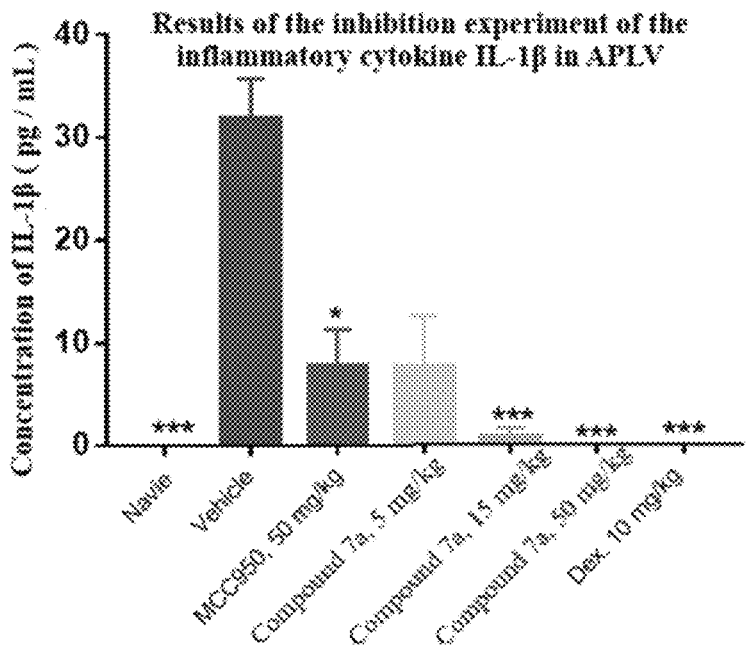
FIG. 2: Results of the inhibition experiment of the inflammatory cytokine IL-1β in APLV.

Compared with healthy control group, an acute inflammatory response in the air pouch of mice was induced by MSU injection, manifested by significantly increased concentrations of inflammatory cytokines IL-6 and IL-1β in APLV. The levels of IL-6 and IL-1β in APLV decreased rapidly after treatment with compound MCC950, compound 7a and dexamethasone. Among them, compound 7a was better than dexamethasone (10 mg/kg dose) in reducing IL-6 at high, medium and low doses, and better than MCC950 (50 mg/kg dose) in reducing IL-6 at the dose of 15 mg/kg and 50 mg/kg. Compound 7a had a significant effect on reducing IL-1β, and the effect on reducing IL-1β at the dose of 15 mg/kg and 50 mg/kg was significantly better than that of MCC950 (50 mg/kg dose), and with extremely low IL-1β levels, reaching the same effect as dexamethasone (10 mg/kg). Results of the inhibition experiment of the inflammatory cytokine IL-6 in APLV are shown in FIG. 1, and results of the inhibition experiment of the inflammatory cytokine IL-1β in APLV are shown in FIG. 2, and p represents significant difference, *: $p<0.05$; : $p<0.01$; *: $p<0.001$.

Conclusion: The compounds of the present disclosure have a good therapeutic effect on the MSU-induced Air Pouch gout model in C57BL/6 mice, and have the potential to treat gout and other diseases related to inflammatory cytokines.

The invention claimed is:

1. A compound represented by formula (II) or a pharmaceutically acceptable salt thereof,

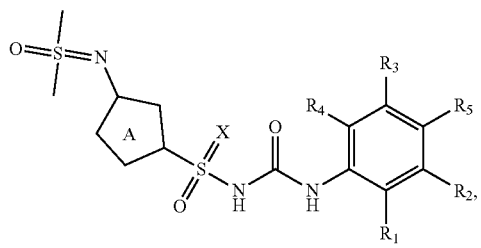

wherein, X is selected from O and $NR_b$;

$R_1$ and $R_4$ are each independently selected from H, $C_{1-3}$ alkyl, phenyl and 5- to 6-membered heteroaryl, and the $C_{1-3}$ alkyl, phenyl and 5- to 6-membered heteroaryl are optionally substituted with 1, 2 or 3 $R_a$;

$R_2$ and $R_3$ are each independently selected from H, $NH_2$, halogen and $C_{1-3}$ alkyl;

or $R_1$ and $R_2$ together with the carbon atoms to which they are attached form $C_{4-5}$ cycloalkyl or $C_{4-5}$ cycloalkenyl;

or $R_3$ and $R_4$ together with the carbon atoms to which they are attached form $C_{4-5}$ cycloalkyl or $C_{4-5}$ cycloalkenyl;

$R_5$ is selected from H, F, Cl, D and CN;

$R_a$ is each independently selected from H, $C_{1-3}$ alkoxy and CN;

$R_b$ is selected from H, CN and $C_{1-3}$ alkyl;

ring A is selected from 5-membered heteroaryl;

the 5- to 6-membered heteroaryl and 5-membered heteroaryl contain 1, 2, 3 or 4 heteroatoms or heteroatom groups independently selected from —NH—, —O—, —S— and N.

2. The compound or the pharmaceutically acceptable salt thereof according to claim 1, wherein, the compound has a structure represented by formula (II-1) or formula (II-2):

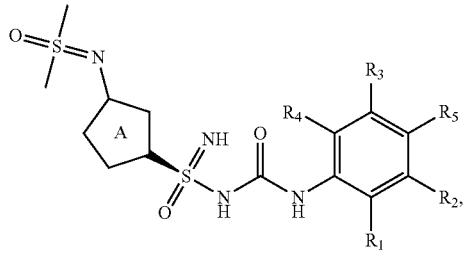

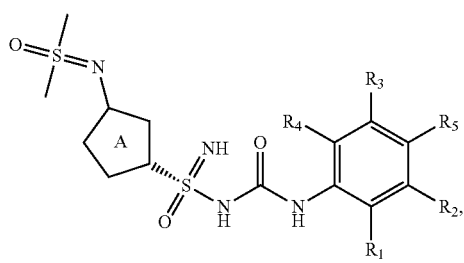

wherein, ring A, $R_1$, $R_2$, $R_3$, $R_4$ and $R_5$ are as defined in claim 1.

3. The compound or the pharmaceutically acceptable salt thereof according to claim 1, wherein, the compound has a structure represented by formula (I-a) or formula (II-a):

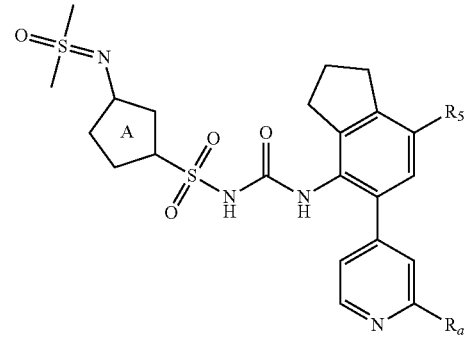

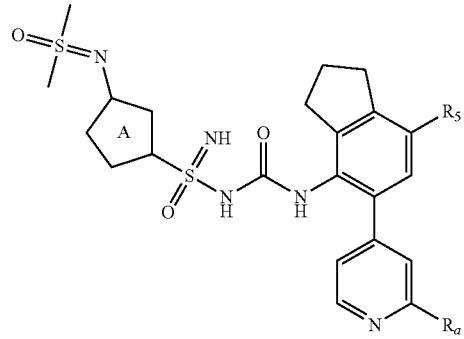

wherein, ring A, $R_a$ and $R_5$ are as defined in claim 1.

4. The compound or the pharmaceutically acceptable salt thereof according to claim 1, wherein, the compound has a structure represented by formula (I-b) or formula (II-b):

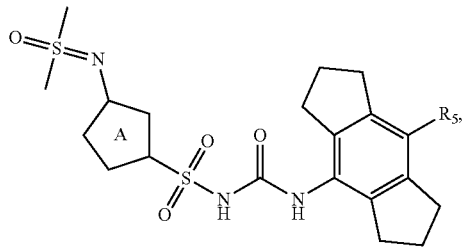
(I-b)

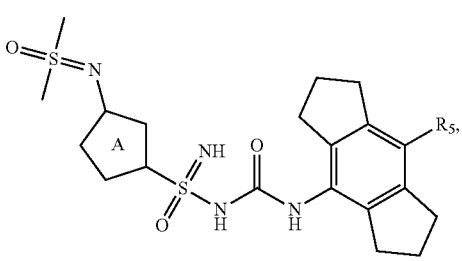
(II-b)

wherein, ring A and $R_5$ are as defined in claim 1.

5. The compound or the pharmaceutically acceptable salt thereof according to claim 1, wherein, the compound has a structure represented by formula (I-c) or formula (II-c):

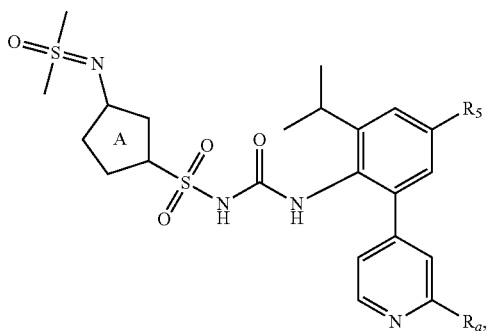
(I-c)

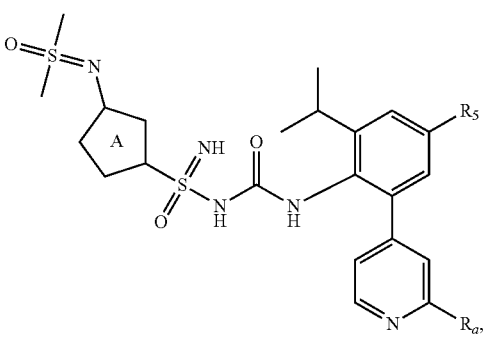
(II-c)

wherein, ring A, $R_a$ and $R_5$ are as defined in claim 1.

6. The compound or the pharmaceutically acceptable salt thereof according to claim 1, wherein, the compound has a structure represented by formula (III):

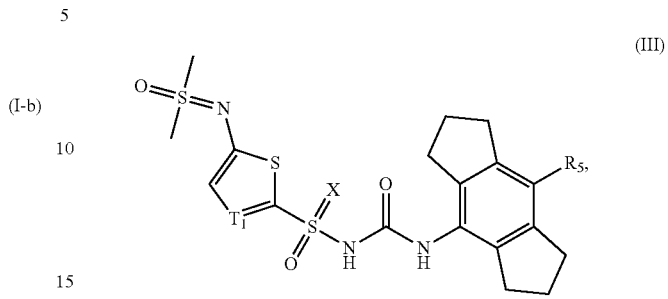
(III)

wherein,
$T_1$ is selected from N and CH;
X and $R_5$ are as defined in claim 1.

7. The compound or the pharmaceutically acceptable salt thereof according to claim 1, wherein, $R_a$ is selected from H, $OCH_3$ and CN.

8. The compound or the pharmaceutically acceptable salt thereof according to claim 1, wherein, $R_1$ is selected from

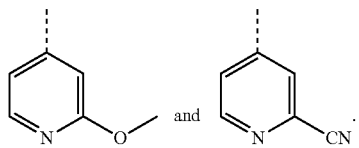

9. The compound or the pharmaceutically acceptable salt thereof according to claim 1, wherein, $R_2$ is selected from H.

10. The compound or the pharmaceutically acceptable salt thereof according to claim 1, wherein, $R_3$ is selected from H.

11. The compound or the pharmaceutically acceptable salt thereof according to claim 1, wherein, $R_4$ is selected from

12. The compound or the pharmaceutically acceptable salt thereof according to claim 1, wherein, $R_1$ and $R_2$ together with the carbon atoms to which they are attached form

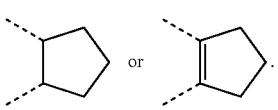

13. The compound or the pharmaceutically acceptable salt thereof according to claim 1, wherein, $R_3$ and $R_4$ together with the carbon atoms to which they are attached form

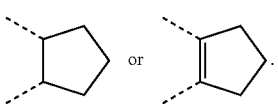

14. The compound or the pharmaceutically acceptable salt thereof according to claim 1, wherein, the structural moiety

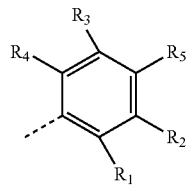

is selected from

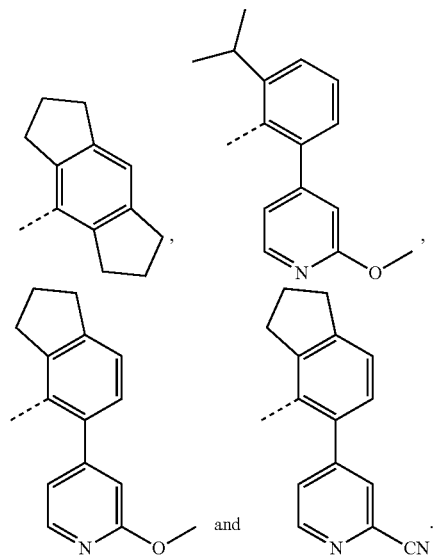

and

15. The compound or the pharmaceutically acceptable salt thereof according to claim 1, wherein, ring A is selected from thienyl and thiazolyl.

16. The compound or the pharmaceutically acceptable salt thereof according to claim 15, wherein, ring A is selected from

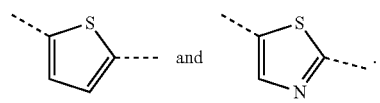

17. A compound represented by the following formula or a pharmaceutically acceptable salt thereof, selected from:

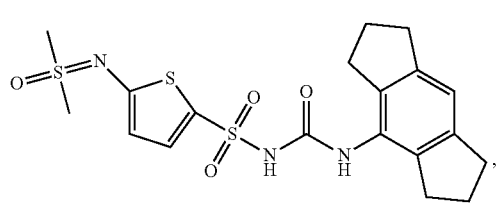

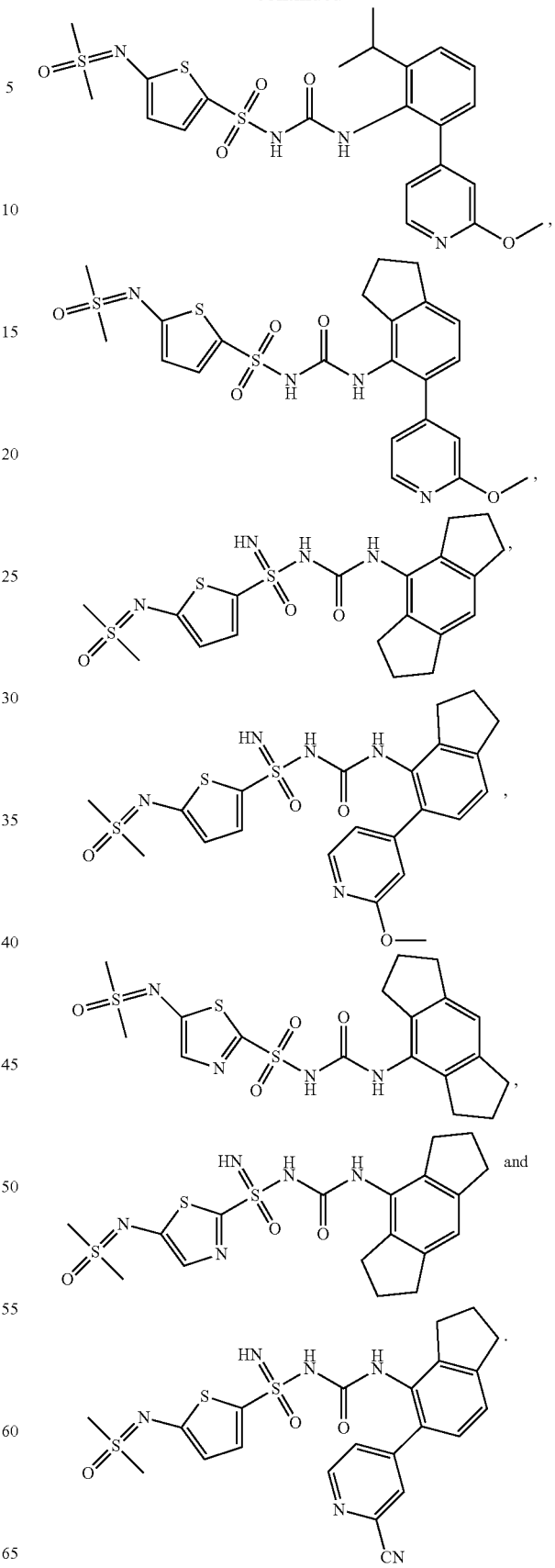

18. The compound or the pharmaceutically acceptable salt thereof according to claim 17, wherein the compound is selected from,

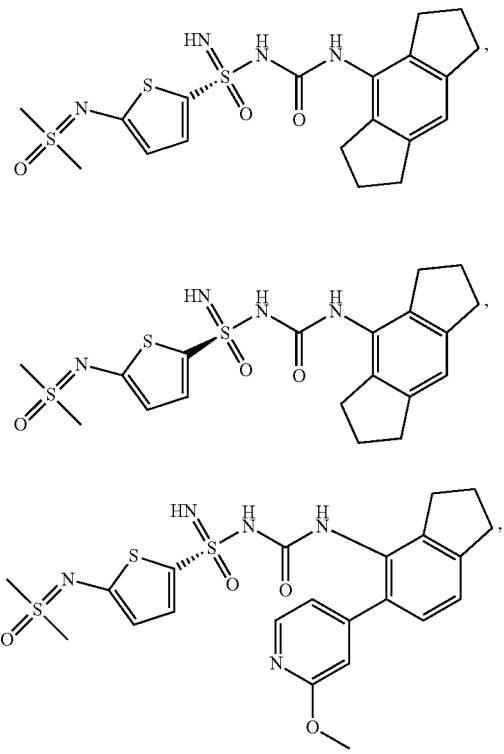

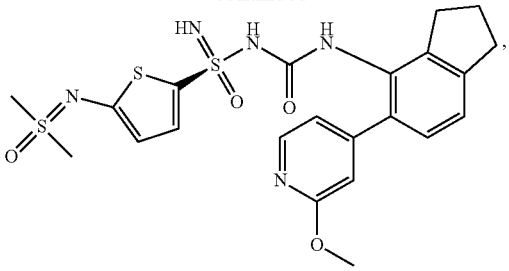

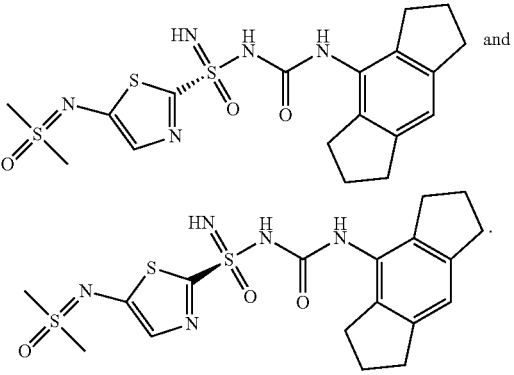

19. A method of inhibiting NLRP3 in a subject in need thereof, comprising: administering an effective amount of the compound or the pharmaceutically acceptable salt thereof according to claim 1 to the subject.

20. A method for treating inflammation in a subject in need thereof, comprising: administering an effective amount of the compound or the pharmaceutically acceptable salt thereof according to claim 1 to the subject.

* * * * *